US011999784B2

(12) United States Patent
Bonnafous et al.

(10) Patent No.: US 11,999,784 B2
(45) Date of Patent: *Jun. 4, 2024

(54) TREATMENT OF PERIPHERAL T CELL LYMPHOMA

(71) Applicant: INNATE PHARMA, Marseilles (FR)

(72) Inventors: Cécile Bonnafous, Marseilles (FR); Hélène Sicard, Marseilles (FR); Renaud Buffet, Boulogne (FR); Mathieu Blery, Marseilles (FR)

(73) Assignee: INNATE PHARMA, Marseilles (FR)

( * ) Notice: Subject to any disclaimer, the term of this patent is extended or adjusted under 35 U.S.C. 154(b) by 1223 days.

This patent is subject to a terminal disclaimer.

(21) Appl. No.: 16/451,051

(22) Filed: Jun. 25, 2019

(65) Prior Publication Data
US 2019/0315857 A1    Oct. 17, 2019

Related U.S. Application Data

(63) Continuation of application No. 14/767,600, filed as application No. PCT/EP2014/052849 on Feb. 13, 2014, now Pat. No. 10,344,087.

(60) Provisional application No. 61/831,792, filed on Jun. 6, 2013, provisional application No. 61/764,639, filed on Feb. 14, 2013.

(51) Int. Cl.
*C07K 16/28* (2006.01)
*C07K 16/30* (2006.01)
*G01N 33/574* (2006.01)

(52) U.S. Cl.
CPC .......... *C07K 16/28* (2013.01); *C07K 16/2803* (2013.01); *C07K 16/3061* (2013.01); *G01N 33/57407* (2013.01); *C07K 2317/73* (2013.01); *C07K 2317/732* (2013.01); *G01N 2333/70503* (2013.01)

(58) Field of Classification Search
None
See application file for complete search history.

(56) References Cited

U.S. PATENT DOCUMENTS

| 10,344,087 | B2 * | 7/2019 | Bonnafous ......... C07K 16/3061 |
| 2008/0274047 | A1 | 11/2008 | Romagne et al. |
| 2011/0250681 | A1 | 10/2011 | Lazar et al. |
| 2012/0288499 | A1 * | 11/2012 | Bensussan ....... G01N 33/57407 435/6.12 |
| 2014/0234342 | A1 | 8/2014 | Narini-Mancinelli et al. |

FOREIGN PATENT DOCUMENTS

| AU | 2012 202 895 | 6/2012 |
| WO | WO 2011/086179 | 7/2011 |
| WO | WO 2012/175613 | 12/2012 |

OTHER PUBLICATIONS

Freud et al. (Am. J Clin. Pathol. 2013 140: 853-866) (Year: 2013).*
Bernardo et al. (Clin. Immunol. 2008 126: 172-179) (Year: 2008).*
Nguyen et al. (Eur. J. Immunol. 2008 38: 2034-2045) (Year: 2008).*
Foss, F. "Evolving therapy of peripheral T-cell lymphoma: 2010 and beyond" *Therapeutic Advances in Hematology*, 2011, vol. 2, No. 3, pp. 161-173.
Hsi, E.D. et al. "CS-1 Is Expressed in Nasal Type NK/T Cell Lymphomas and Angioimmunoblastic T-Cell Lymphomas: Implications for Targeted Therapy with Elotuzumab (HuLuc63)" *Blood*, Dec. 9, 2008, vol. 112, No. 11, Abstract 1779, ASH Annual Meeting Abstracts, p. 1.
Weidmann, E. et al. "A Phase II Immunochemotherapy Study with Alemtuzumab, Fludarabine, Cyclophosphamide, and Doxorubicin (Campath-FCD) in Peripheral T-Cell Lymphomas" *Blood*, Nov. 11, 2006, vol. 108, No. 11, Abstract 2721, ASH Annual Meeting Abstracts, p. 1.
Yamamoto, K. et al. "Phase I Study of KW-0761, a Defucosylated Humanized Anti-CCR4 Antibody, in Relapsed Patients With Adult T-Cell Leukemia-Lymphoma and Peripheral T-Cell Lymphoma" *Journal of Clinical Oncology*, Mar. 20, 2010, vol. 28, No. 9, pp. 1591-1598.
Berglund, L. et al. "The epitope space of the human proteome" *Protein Science*, 2008, pp. 606-613, vol. 17.
Bensussan, A. et al. "Expression and Function of the Natural Cytotoxicity Receptor NKp46 on Circulating Malignant CD4+ T Lymphocytes of Sezary Syndrome Patients" *Journal of Investigative Dermatology*, 2011, pp. 969-976, vol. 131.
Iqbal, J. et al. "Natural killer cell lymphoma shares strikingly similar molecular features with a group of non-hepatosplenic γδ T-cell lymphoma and is highly sensitive to a novel aurora kinase A inhibitor in vitro" *Leukemia*, 2011, pp. 348-358, vol. 25.
Lymphoma, "Peripheral T-Cell Lymphoma (PTCL)" 2016, http://www.lymphoma.org/site/pp.asp?c=bkL TKaOQLmK8E&b=6300159, pp. 1-4.
Padlan, E. A. "X-Ray Crystallography of Antibodies" *Advances in Protein Chemistry*, 1996, pp. 57-133, vol. 49.
Inagaki, N. et al. "Enteropathy-Type T-Cell Lymphoma Expressing NK-Cell Intraepithelial Lymphocyte (NK-IEL) Phenotype" *Leukemia & Lymphoma*, Jul. 2004, pp. 1471-1474, vol. 45, No. 7.
Rubio-Tapia, A. et al. "Classification and Management of Refractory Celiac Disease" *Gut*, Apr. 2010, pp. 547-557, vol. 59, No. 4.
Sanchez, D. et al. "Anti-calreticulin immunoglobulin A (IgA) antibodies in refractory celiac disease" *Clinical and Experimental Immunology*, 2008, pp. 351-359, vol. 153.

(Continued)

*Primary Examiner* — Peter J Reddig
(74) *Attorney, Agent, or Firm* — SALIWANCHIK, LLOYD & EISENSCHENK

(57) ABSTRACT

The present disclosure relates to methods for the treatment, prevention and diagnosis of peripheral T-cell lymphoma using compounds that specifically bind NKp46. Included in particular are compounds that bind NKp46 and deplete tumor cells that express NKp46 at their surface, and pharmaceutical compositions comprising the same. The disclosure also relates to the use of antibodies that specifically bind NKp46 in diagnostic and theranostic assays in the detection and treatment of peripheral T-cell lymphoma.

1 Claim, 2 Drawing Sheets

Specification includes a Sequence Listing.

(56) References Cited

OTHER PUBLICATIONS

Corada, M. et al. "Monoclonal antibodies directed to different regions of vascular endothelial cadherin extracellular domain affect adhesion and clustering of the protein and modulate endothelial permeability" *Blood*, Mar. 15, 2001, pp. 1679-168, vol. 97, No. 6.
Carter, P. J. "Potent antibody therapeutics by design" *Nature Reviews*, May 2006, pp. 343-347, vol. 6.
NORD National Organization for Rare Disorders, 2016, https://rarediseases.org/rare-diseases/refractory-celiac-disease, pp. 1-13.
Arps, D. P. et al. "Classic Versus Type II Enteropathy-Associated T-Cell Lymphoma" Arch *Pathol Lab Med.*, Sep. 2013, pp. 1227-1231, vol. 137.

* cited by examiner

SEQUENCE LISTING

```
<160> NUMBER OF SEQ ID NOS: 1

<210> SEQ ID NO 1
<211> LENGTH: 304
<212> TYPE: PRT
<213> ORGANISM: homo sapiens

<400> SEQUENCE: 1

Met Ser Ser Thr Leu Pro Ala Leu Leu Cys Val Gly Leu Cys Leu Ser
1               5                   10                  15

Gln Arg Ile Ser Ala Gln Gln Thr Leu Pro Lys Pro Phe Ile Trp
            20                  25                  30

Ala Glu Pro His Phe Met Val Pro Lys Glu Lys Gln Val Thr Ile Cys
            35                  40                  45

Cys Gln Gly Asn Tyr Gly Ala Val Glu Tyr Gln Leu His Phe Glu Gly
        50                  55                  60

Ser Leu Phe Ala Val Asp Arg Pro Lys Pro Glu Arg Ile Asn Lys
65                  70                  75                  80

Val Lys Phe Tyr Ile Pro Asp Met Asn Ser Arg Met Ala Gly Gln Tyr
                85                  90                  95

Ser Cys Ile Tyr Arg Val Gly Glu Leu Trp Ser Glu Pro Ser Asn Leu
            100                 105                 110

Leu Asp Leu Val Val Thr Glu Met Tyr Asp Thr Pro Thr Leu Ser Val
            115                 120                 125

His Pro Gly Pro Glu Val Ile Ser Gly Glu Lys Val Thr Phe Tyr Cys
        130                 135                 140

Arg Leu Asp Thr Ala Thr Ser Met Phe Leu Leu Leu Lys Glu Gly Arg
145                 150                 155                 160

Ser Ser His Val Gln Arg Gly Tyr Gly Lys Val Gln Ala Glu Phe Pro
                165                 170                 175

Leu Gly Pro Val Thr Thr Ala His Arg Gly Thr Tyr Arg Cys Phe Gly
            180                 185                 190

Ser Tyr Asn Asn His Ala Trp Ser Phe Pro Ser Glu Pro Val Lys Leu
            195                 200                 205

Leu Val Thr Gly Asp Ile Glu Asn Thr Ser Leu Ala Pro Glu Asp Pro
        210                 215                 220

Thr Phe Pro Ala Asp Thr Trp Gly Thr Tyr Leu Leu Thr Thr Glu Thr
225                 230                 235                 240

Gly Leu Gln Lys Asp His Ala Leu Trp Asp His Thr Ala Gln Asn Leu
                245                 250                 255

Leu Arg Met Gly Leu Ala Phe Leu Val Leu Val Ala Leu Val Trp Phe
            260                 265                 270

Leu Val Glu Asp Trp Leu Ser Arg Lys Arg Thr Arg Glu Arg Ala Ser
            275                 280                 285

Arg Ala Ser Thr Trp Glu Gly Arg Arg Arg Leu Asn Thr Gln Thr Leu
        290                 295                 300
```

TREATMENT OF PERIPHERAL T CELL LYMPHOMA

CROSS-REFERENCE TO RELATED APPLICATIONS

This application is a continuation of U.S. application Ser. No. 14/767,600, filed Aug. 13, 2015, now U.S. Pat. No. 10,344,087, which is the U.S. national stage application of International Patent Application No. PCT/EP2014/052849, filed Feb. 13, 2014, which claims the benefit of U.S. Provisional Application No. 61/764,639, filed Feb. 14, 2013, and U.S. Provisional Application No. 61/831,792, filed Jun. 6, 2013, the disclosures of which are incorporated herein by reference in their entirety, including any drawings.

REFERENCE TO SEQUENCE LISTING

The present application is being filed along with a Sequence Listing in electronic format. The Sequence Listing is provided as a file entitled "NKp46-2 PCT_ST25", created 12 Feb. 2014, which is 3 KB in size. The information in the electronic format of the Sequence Listing is incorporated herein by reference in its entirety.

FIELD OF THE INVENTION

This invention relates to the use of NKp46-targeting agents for the diagnosis and treatment of aggressive lymphomas.

BACKGROUND OF THE INVENTION

NK cell activity is regulated by a complex mechanism that involves both activating and inhibitory signals. Several distinct NK-specific receptors have been identified that play an important role in the NK cell-mediated recognition and killing of HLA Class I deficient target cells. Natural Cytotoxicity Receptors (NCR) refers to a class of activating receptor proteins, and the genes expressing them, that are specifically expressed in NK cells. Examples of NCRs include NKp30, NKp44, and NKp46 (see, e.g., Lanier (2001) Nat Immunol 2:23-27, Pende et al. (1999) J Exp Med. 190:1505-1516, Cantoni et al. (1999) J Exp Med. 189:787-796, Sivori et al (1997) J Exp Med. 186:1129-1136, Pessino et al. (1998) J Exp Med. 188(5):953-60, and Mandelboim et al. (2001) Nature 409:1055-1060, the entire disclosures of which are herein incorporated by reference). These receptors are members of the Ig superfamily, and their cross-linking, induced by specific mAbs, leads to a strong NK cell activation resulting in increased intracellular $Ca^{++}$ levels, triggering of cytotoxicity, and lymphokine release, and an activation of NK cytotoxicity against many types of target cells. The expression of NCRs, and NKp46 in particular, is reported as limited to NK cells.

Peripheral T-cell non-Hodgkin's lymphomas (PTCLs) account for 15% to 20% of aggressive lymphomas and 7% to 10% of all the non-Hodgkin's lymphomas (NHLs) in Western countries. They usually occur in middle-aged to elderly patients, and presenting features are characterized by a disseminated disease in 68% of the patients, with systemic symptoms in nearly half of them (45%), bone marrow (BM) involvement in a quarter (25.8%), and extranodal disease in a third (37%). Despite aggressive therapy, more than half the patients die of their disease. While certain distinctive disease entities have improved prognostics if treated, the prognosis for many aggressive PTCLs remains relatively unchanged by the use of second- and third-generation chemotherapy regimens and 5-year overall survival (OS) still remains between 25% and 47% for PTCL-NOS, for example.

Consequently, there is a need in the art for improved benefit to patients having PTCLs.

SUMMARY OF THE INVENTION

The present inventors have discovered that NKp46 is expressed on peripheral T-cell lymphomas (PTCLs), particularly non-cutaneous PTCLs. In NKp46-positive PTCLs, NKp46 is expressed on the cell surface and at levels sufficient to permit targeting with NKp46-binding antibodies (e.g., as assessed by immunohistochemistry). NKp46 is expressed on few other tissues (only on a small fraction of NK cells), permitting NKp46 to serve as a marker and target for the detection and treatment of peripheral T-cell lymphomas, particularly aggressive and/or advanced T-cell lymphomas, e.g., aggressive and/or advanced nodal or extranodal peripheral T-cell lymphomas. Accordingly, in one embodiment, a method is provided for treating or preventing a peripheral T-cell lymphoma in an individual, the method comprising administering to an individual a therapeutically active amount of a compound that binds an NKp46 polypeptide. In one aspect a composition is provided comprising a compound that binds an NKp46 polypeptide, for use in the treatment or prevention of peripheral T-cell lymphoma. In one aspect the compound that binds an NKp46 polypeptide is a compound that depletes a cell that expresses NKp46 at its surface, e.g., a PTCL cell that expresses NKp46. In one aspect the compound is a depleting anti-NKp46 antibody. In one embodiment a compound is provided that binds an NKp46 polypeptide and depletes NKp46-expressing tumor cells, for use in the treatment or prevention of a PTCL in an individual. Optionally said treatment or prevention comprises administration of a compound that binds an NKp46 polypeptide to an individual having a PTCL. In one embodiment of any of the therapeutic uses or PTCL treatment or prevention methods herein, the individual has an NK/T-lymphoma. In one embodiment of any of the therapeutic uses or PTCL treatment or prevention methods herein, the individual has an enteropathy-associated T-cell lymphoma (EATL). In one embodiment of any of the therapeutic uses or PTCL treatment or prevention methods herein, the individual has an anaplastic large cell lymphoma (ALCL). In one embodiment of any of the therapeutic uses or PTCL treatment or prevention methods herein, the individual has a PTCL-NOS. In one embodiment of any of the therapeutic uses or PTCL treatment or prevention methods herein, the treatment or prevention of a PTCL (e.g., an EATL, an ALCL, or a PTCL-NOS) in an individual comprises:

a) determining the NKp46 polypeptide status of malignant cells within the individual having a PTCL, and b) upon a determination that the patient that an NKp46 polypeptide prominently expressed on the surface of malignant cells, administering to the individual said compound that binds an NKp46 polypeptide.

In one embodiment of any the treatment methods or uses herein, NK/T lymphoma, nasal type, is treated, and the method does not require (e.g., is free of, or does not use, or does not comprise) a step of: determining the NKp46 polypeptide status of malignant cells within the individual having a PTCL prior to administration of a compound that binds an NKp46 polypeptide.

Additionally, it has been found that patients having more advanced PTCLs have acquired NKp46 expression while PTCLs at earlier stages may be NKp46-negative. Accordingly, in one embodiment, a method is provided for treating an individual having an advanced (e.g., stage IV or higher) peripheral T-cell lymphoma, the method comprising administering to the individual a therapeutically active amount of a compound that binds an NKp46 polypeptide.

In another embodiment a method is provided combining an NKp46 detection step to identify patients having NKp46+ tumors; these patients can thereafter be treated with an NKp46-binding agent. Such method permits NKp46 therapy to be directed to suitable patients without reliance on a disease staging. Such method also helps permit the prevention of advanced PTCL (e.g., prevention of progressing of PTCL to an advanced stage, e.g., stage IV) because patients can be treated as NKp46 appears. In particular, since not all patients have tumors that are positive for NKp46 expression, the method has the advantage of permitting selection of individual patients having tumors that are expected to be responsive to treatment with a compound that binds an NKp46 polypeptide.

In a further aspect, it has been found that patients with NKp46-positive PTCL-NOS can have tumors that are CD30-negative (tumor cells do not express CD30 on their surface). Thus, methods are provided of treating a CD30-negative PTCL, e.g., a PTCL-NOS, comprising administering a compound that binds an NKp46 polypeptide to a patient having a CD30-negative PTCL. In another embodiment of treating an individual having a PTCL, the method comprises administering a compound that binds an NKp46 polypeptide to an individual having a PTCL who is refractive to treatment with an anti-CD30 antibody. In other embodiments, when PTCLs are CD30-positive (e.g., anaplastic large cell lymphomas which broadly express CD30, certain PTCL-NOS), a compound that binds an NKp46 polypeptide can be administered in combination with an anti-CD30 antibody (e.g., a depleting anti-CD30 antibody, for example an anti-CD30 antibody linked to a toxic moiety).

In one embodiment, a method is provided for detecting a peripheral T-cell lymphoma in an individual, the method comprising detecting an NKp46 nucleic acid or polypeptide in a biological sample (e.g., on a cell) from an individual. In one embodiment, a method is provided for detecting an aggressive or advanced (e.g., stage IV or higher) peripheral T cell lymphoma in an individual, the method comprising detecting an NKp46 nucleic acid or polypeptide in a biological sample (e.g., on a cell) from an individual. A determination that a biological sample expresses NKp46 indicates that the patient has a peripheral T-cell lymphoma (or advanced/aggressive PTCL). In one embodiment, the method comprises determining the level of expression of an NKp46 nucleic acid or polypeptide in a biological sample and comparing the level to a reference level (e.g., a value, weak cell surface staining, etc.) corresponding to a healthy individual. A determination that a biological sample expresses an NKp46 nucleic acid or polypeptide at a level that is increased compared to the reference level indicates that the patient has a peripheral T-cell lymphoma. Optionally, detecting an NKp46 polypeptide in a biological sample comprises detecting the NKp46 polypeptide expressed on the surface of a malignant lymphocyte.

In one embodiment, a method is provided comprising:
(a) determining whether an individual has an advanced and/or aggressive peripheral T-cell lymphoma; and
(b) if the individual has an advanced and/or aggressive peripheral T-cell lymphoma, treating the individual with a therapeutically active amount of a compound that binds an NKp46 polypeptide.

In one embodiment, a method is provided comprising: (a) determining whether an individual has a peripheral T-cell lymphoma; and (b) if the individual has a peripheral T-cell lymphoma, determining whether the individual has peripheral T-cell lymphoma cells that express an NKp46 polypeptide. The method may optionally further comprise treating the individual with a therapeutically active amount of a compound that binds an NKp46 polypeptide if the individual has peripheral T-cell lymphoma cells that express NKp46 on their surface.

In one embodiment, a method is provided comprising:
(a) determining whether an individual has peripheral T cell lymphoma cells that express an NKp46 polypeptide on their surface; and
(b) if the individual has peripheral T-cell lymphoma cells that express NKp46 on their surface, treating the individual with a therapeutically active amount of a compound that binds an NKp46 polypeptide.

In one embodiment, a method is provided comprising treating an individual having a CD30-negative PTCL. In one embodiment, the method comprises:
(a) determining whether an individual (e.g., an individual with advanced PTCL) has peripheral T-cell lymphoma cells that express CD30 on their surface, optionally further determining whether an individual has peripheral T-cell lymphoma cells that express NKp46 on their surface; and
(b) if the individual has peripheral T-cell lymphoma cells that do not express CD30 on their surface, optionally wherein the individual has peripheral T-cell lymphoma cells that express an NKp46 polypeptide on their surface, treating the individual with a therapeutically active amount of a compound that binds an NKp46 polypeptide.

In one embodiment, a method is provided comprising treating an individual having a CD30-positive PTCL. In one embodiment, the method comprises:
(a) determining whether an individual (e.g., an individual with advanced PTCL) has peripheral T-cell lymphoma cells that express CD30 on their surface, and further determining whether the individual has peripheral T-cell lymphoma cells that express NKp46 on their surface; and
(b) if the individual has peripheral T-cell lymphoma cells that express CD30 on their surface, and the individual has peripheral T-cell lymphoma cells that express an NKp46 polypeptide on their surface, treating the individual with a therapeutically active amount of a compound that binds an NKp46 polypeptide and with a therapeutically active amount of an anti-CD30 antibody.

In one embodiment of any of the methods, determining whether an individual has peripheral T-cell lymphoma cells that express an NKp46 polypeptide comprises obtaining a biological sample from the individual that comprises peripheral T-cell lymphoma cells, bringing said cells into contact with an antibody that binds an NKp46 polypeptide, and detecting whether cells express NKp46 on their surface.

Optionally, in any embodiment, determining whether an individual has peripheral T-cell lymphoma cells that express NKp46 comprises conducting an immunohistochemistry assay. Optionally, determining whether an individual has peripheral T-cell lymphoma cells that express NKp46 comprises conducting a flow cytometry assay. Both IHC and flow cytometry can detect surface expression of NKp46.

A method is also provided of treating a patient with a PTCL, the method comprising: a) determining the NKp46 polypeptide status of malignant cells (e.g., PTCL cells) within the patient, e.g., determining whether an NKp46 polypeptide is prominently expressed on the surface of said malignant cells, and b) administering a compound to the patient that specifically binds to an NKp46 polypeptide that is prominently expressed in said malignant cells (e.g., prominently expressed on the surface of malignant cells). Optionally, determining the NKp46 polypeptide status comprises determining whether an NKp46 polypeptide is prominently expressed on the surface of said malignant cells. Optionally, determining whether an NKp46 polypeptide is prominently expressed on the surface of said malignant cells comprises obtaining from the individual a biological sample that comprises peripheral T-cell lymphoma cells, bringing said cells into contact with an antibody that binds an NKp46 polypeptide, and detecting cells that express NKp46 (e.g., determining the number or portion of cells that express NKp46). Thus, in one embodiment, the disclosure provides a method for detecting NKp46 expression in an individual having refractory celiac disease (RCD) and treating said individual comprising: a) obtaining a biological sample from the individual, said biological sample comprising RCD cells, contacting said RCD cells with an antibody that binds NKp46 polypeptide, and detecting NKp46 polypeptide expression on the surface of said cells; and b) treating individuals expressing NKp46 polypeptide on RCD cells with anti-NKp46 antibodies.

Preferably the compound that binds an NKp46 polypeptide is a compound that causes the death of an NKp46-expressing cell. Optionally, the compound that binds an NKp46 polypeptide is a polypeptide, optionally an antibody (e.g., monoclonal antibody), that binds an NKp46 polypeptide, optionally a polypeptide or other compound that is a natural ligand of NKp46. Optionally, the antibody is a depleting antibody. Optionally, the antibody is an antibody that directs ADCC and/or CDC toward an NKp46-expressing cell. Optionally, the compound that binds an NKp46 polypeptide delivers a cytotoxic agent (e.g., small molecule) to an NKp46-expressing cell, e.g., an anti-NK46 antibody linked to a toxic moiety.

Optionally, the compound that binds an NKp46 polypeptide is administered between once daily and once per month. Optionally, the composition is administered as monotherapy. Optionally, the composition is administered in combination with a second therapeutic agent. Optionally, the composition is administered in combination with an anti-cancer agent.

In one embodiment, a method is provided of producing a composition for the treatment of peripheral T-cell lymphoma or for use in the prevention of peripheral T-cell lymphoma in a mammalian subject, said method comprising the steps of: a) providing a plurality of test compositions; b) testing each compound for the ability to bind NKp46 and/or cause the depletion of NKp46-expressing cells; and c) selecting a compound which binds an NKp46 polypeptide and/or causes the depletion of NKp46-expressing cells as suitable for the treatment of peripheral T-cell lymphoma or for use in the prevention of peripheral T-cell lymphoma.

Optionally, the method further comprises producing a quantity of the compound selected in step c) and/or formulation a quantity of the compound selected in step c) with a pharmaceutically acceptable excipient.

Optionally, step b) further comprises testing said test composition for the ability to direct ADCC and/or CDC toward an NKp46-expressing cell, e.g., a peripheral T-cell lymphoma cell.

In one embodiment, a method is provided comprising:
(a) determining whether an individual has a peripheral T-cell lymphoma; and
(b) if the individual has a peripheral T-cell lymphoma, treating the individual with a therapeutically active amount of a compound that binds an NKp46 polypeptide.

In one embodiment, determining whether an individual has a peripheral T-cell lymphoma is made according to standard medical guidelines.

In one embodiment, determining whether an individual has a peripheral T-cell lymphoma comprises identifying a population of abnormal cells or abnormal numbers of cells. Optionally, said identification is by flow cytometry. Optionally, the method further comprises sorting or isolating the population of abnormal cells.

In one embodiment, determining whether an individual has a peripheral T-cell lymphoma comprises detecting cytogenetic aberrations (e.g., assessing karyotype).

In one embodiment, determining whether an individual has a peripheral T-cell lymphoma comprises sorting the population of abnormal cells, and contacting nucleic acid isolated from the sorted cells with one or more oligonucleotides, wherein the contacting determines the presence of a neoplastic genetic marker, thereby detecting the presence of peripheral T-cell lymphoma.

In one embodiment, determining whether an individual has a peripheral T-cell lymphoma comprises assessing the levels of a serum protein in the individual.

Optionally, the method further comprises a step of assessing, following treatment with a compound that binds an NKp46 polypeptide, whether the individual has an amelioration in peripheral T-cell lymphoma, e.g., whether the individual has decreased numbers of peripheral T-cell lymphoma cells.

In one embodiment of any aspect herein, the PTCL is an aggressive and/or advanced PTCL. In one embodiment, the PTCL is aggressive non-cutaneous PTCL. In one embodiment, the PTCL is PTCL-NOS (also referred to as PCTL-U). In one embodiment, the PTCL is a nodal (e.g., primarily nodal) PTCL, for example a PTCL-NOS, AITL, or ALCL (ALK+ or ALK−). In one embodiment, the PTCL is an anaplastic large cell lymphoma (ALCL), optionally an ALK-negative ALCL. In one embodiment, the PTCL is an angio-immunoblastic T-cell lymphoma (AITL), optionally a cutaneous AITL, optionally a non-cutaneous AITL. In one embodiment, a PTCL may be an aggressive, non-cutaneous, primarily nodal PCTL. In one embodiment, the PTCL is an extranodal (e.g., primarily extranodal) PTCL. In one example a PTCL may be an aggressive, non-cutaneous, extranodal PCTL. In one embodiment, the PTCL is an adult T-cell leukemia or lymphoma (ATL), e.g., an HTLV+ ATL. In one embodiment, the PTCL is an orthovisceral extranodal disease, e.g., NK−/T-cell lymphoma or an enteropathy-associated T-cell lymphoma. In one embodiment, the PTCL is an extranodal NK−/T-cell lymphoma, nasal type. In one embodiment, the PTCL is an enteropathy-associated T-cell lymphoma (EATL).

In one embodiment of any aspect herein, the PTCL is a CD30-positive PTCL and the anti-NKp46 antibody is administered in combination with an anti-CD30 antibody. In one embodiment of any aspect herein, the PTCL is a CD4-positive PTCL and the anti-NKp46 antibody is administered in combination with an anti-CD4 antibody.

In one embodiment of any aspect herein, the PTCL is characterized by absence of NK cell-associated or NK-specific markers, e.g., CD56 and/or CD57. In one embodiment of any aspect herein, the PTCL is characterized by the presence of NK cell-associated or NK-specific markers, e.g., CD56 and/or CD57.

These aspects are more fully described in, and additional aspects, features, and advantages will be apparent from, the description of the invention provided herein.

DESCRIPTION OF THE INVENTION

Figure 1:
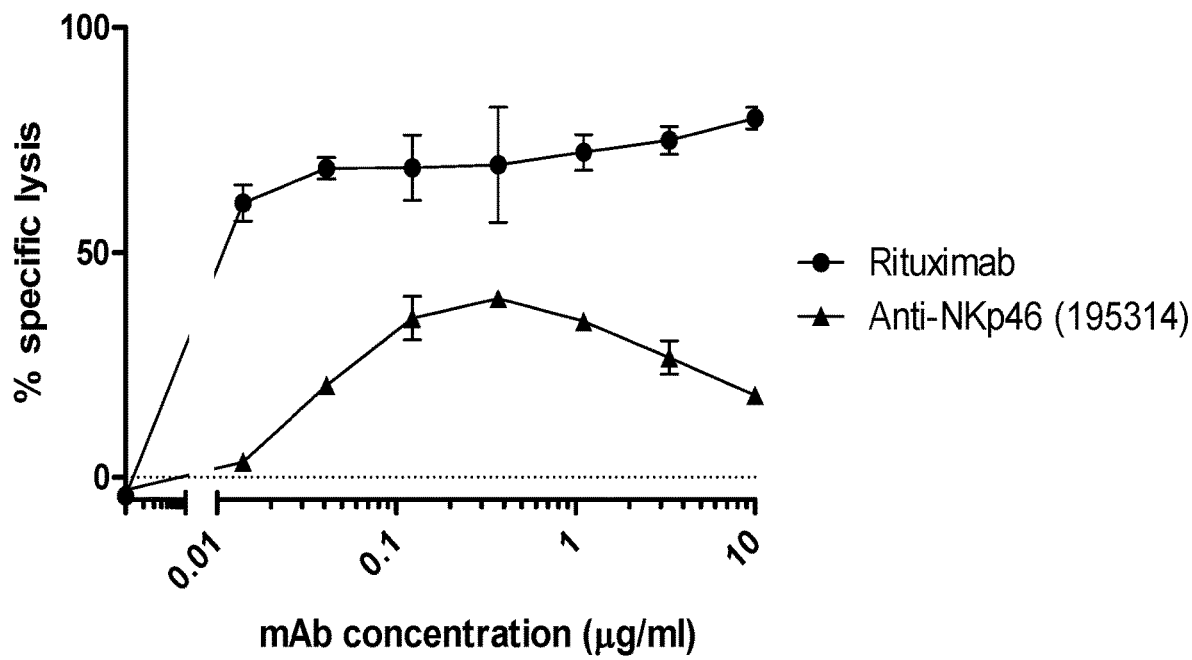
FIG. 1 shows antibody 195314 (as well as positive control rituximab) induced specific lysis of NKp46-transfected 721.221 cells in an ADCC assay, using human KHYG-1 murine FcyRIV NK cell lines.

The identification expression of NKp46 polypeptides at the surface of malignant PTCL cells permits the development of therapeutic agents that are able to directly and specifically target pathogenic cells, as well as diagnostic agents that can be used to diagnose PTCL.

Methods are provided of using the antigen-binding compounds; for example, a method is provided for inhibiting PTCL cell proliferation or activity, for delivering a molecule to a PTCL cell (e.g., a toxic molecule, a detectable marker, etc.), for targeting, identifying or purifying a cell, for depleting, killing or eliminating a cell, or for reducing cell proliferation, the method comprising exposing a cell, such as a PTCL cell which expresses an NKp46 polypeptide, to an antigen-binding compound that binds an NKp46 polypeptide. It will be appreciated that for the purposes herein, "cell proliferation" can refer to any aspect of the growth or proliferation of cells, e.g., cell growth, cell division, or any aspect of the cell cycle. The cell may be in a cell culture (in vitro) or in a mammal (in vivo), e.g., a mammal suffering from PTCL. Also provided is a method for inducing the death of a cell or inhibiting the proliferation or activity of a PTCL cell which expresses an NKp46 polypeptide, comprising exposing the cell to an antigen-binding compound that binds an NKp46 polypeptide in an amount effective to induce death and/or inhibit the proliferation of the cell.

Antibodies specific for NKp46 can be used for a range of purposes for the diagnosis or treatment of PTCL, including purifying NKp46 or NKp46-expressing cells in patients having PTCL, suspected of having PTCL or susceptible to PTCL, targeting NKp46-expressing cells for destruction in vivo, or specifically labeling/binding NKp46 in vivo, ex vivo, or in vitro, in cells of patients having PTCL, suspected of having PTCL or susceptible to PTCL, including in methods such as immunoblotting, IHC analysis (e.g., on frozen tissue samples from biopsies), FACS analysis, and immunoprecipitation.

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

Whenever within this whole specification "treatment of PTCL" or the like is mentioned with reference to an anti-NKp46 binding agent (e.g., antibody), there is meant: (a) method of treatment of PTCL, said method comprising the step of administering (for at least one treatment) an anti-NKp46 binding agent (preferably in a pharmaceutically acceptable carrier material) to an individual, a mammal, or especially a human in need of such treatment, in a dose that allows for the treatment of PTCL (a therapeutically effective amount), preferably in a dose (amount) as specified herein; (b) the use of an anti-NKp46 binding agent for the treatment of PTCL, or an anti-NKp46 binding agent for use in said treatment (especially in a human); (c) the use of an anti-NKp46 binding agent for the manufacture of a pharmaceutical preparation for the treatment of PTCL, a method of using an anti-NKp46 binding agent for the manufacture of a pharmaceutical preparation for the treatment of PTCL, comprising admixing an anti-NKp46 binding agent with a pharmaceutically acceptable carrier, or a pharmaceutical preparation comprising an effective dose of an anti-NKp46 binding agent that is appropriate for the treatment of PTCL; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody" as used herein refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well-known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein-described antibodies.

The term "specifically binds to" means that an antibody can bind preferably in a competitive binding assay to the binding partner, e.g., NKp46, as assessed using either recombinant forms of the proteins, epitopes therein, or native proteins present on the surface of isolated target cells.

Competitive binding assays and other methods for determining specific binding are further described below and are well-known in the art.

When an antibody is said to "compete with" a particular monoclonal antibody, it means that the antibody competes with the monoclonal antibody in a binding assay using either recombinant NKp46 molecules or surface-expressed NKp46 molecules. For example, if a test antibody reduces the binding of Bab281, 9E2 or 195314 to an NKp46 polypeptide or NKp46-expressing cell in a binding assay, the antibody is said to "compete" respectively with Bab281, 9E2 or 195314.

The term "affinity" as used herein means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y. 1988), Coligan et al., eds., Current Protocols in Immunology, Greene Publishing Assoc. and Wiley Interscience, N.Y. (1992, 1993), and Muller, Meth. Enzymol. 92:589-601 (1983), which references are entirely incorporated herein by reference. One standard method well-known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen-binding antibody or peptide, i.e., amino acid residues within the "footprint" of the antibody. It is the simplest form or smallest structural area on a complex antigen molecule that can combine with, e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "immunogenic fragment" refers to any polypeptidic or peptidic fragment that is capable of eliciting an immune response such as (i) the generation of antibodies binding said fragment and/or binding any form of the molecule comprising said fragment, including the membrane-bound receptor and mutants derived therefrom, or (ii) the stimulation of a T-cell response involving T-cells reacting to the bi-molecular complex comprising any MHC molecule and a peptide derived from said fragment. Alternatively, an immunogenic fragment also refers to any construction capable of eliciting an immune response as defined above, such as a peptidic fragment conjugated to a carrier protein by covalent coupling, or a chimeric recombinant polypeptide construct comprising said peptidic fragment in its amino acid sequence, and specifically includes cells transfected with a cDNA of which the sequence comprises a portion encoding said fragment.

The term "depleting", "deplete" or "depletion", with respect to NKp46-expressing cells, means a process, method, or compound that can kill, eliminate, lyse or induce such killing, elimination or lysis, so as to negatively affect the number of NKp46-expressing cells present in a sample or in a subject.

The terms "immunoconjugate", "antibody conjugate", "antibody drug conjugate", and "ADC" are used interchangeably and refer to an antibody that is conjugated to another moiety (e.g., any non-antibody moiety, a therapeutic agent or a label).

The term "agent" is used herein to denote a chemical compound, a mixture of chemical compounds, a biological macromolecule, or an extract made from biological materials. The term "therapeutic agent" refers to an agent that has biological activity.

The terms "toxic agent", "toxic moiety" and "cytotoxic agent" encompass any compound that can slow down, halt, or reverse the proliferation of cells, decrease their activity in any detectable way, or directly or indirectly kill them. Preferably, cytotoxic agents cause cell death primarily by interfering directly with the cell's functioning, and include, but are not limited to, alkylating agents, tumor necrosis factor inhibitors, DNA intercalators, microtubule inhibitors, kinase inhibitors, proteasome inhibitors and topoisomerase inhibitors. A "toxic payload" as used herein refers to a sufficient amount of cytotoxic agent which, when delivered to a cell, results in cell death. Delivery of a toxic payload may be accomplished by administration of a sufficient amount of immunoconjugate comprising an antibody or antigen-binding fragment and a cytotoxic agent. Delivery of a toxic payload may also be accomplished by administration of a sufficient amount of an immunoconjugate comprising a cytotoxic agent, wherein the immunoconjugate comprises a secondary antibody or antigen-binding fragment thereof which recognizes and binds an (anti-NKp46) antibody or antigen-binding fragment.

The term "human-suitable", with respect to an antibody, refers to any antibody, derivatized antibody, or antibody fragment that can be safely used in humans for, e.g., the therapeutic methods described herein. Human-suitable antibodies include all types of humanized, chimeric, or fully human antibodies, or any antibodies in which at least a portion of the antibodies is derived from humans or otherwise modified so as to avoid the immune response that is generally provoked when native non-human antibodies are used.

For the purposes herein, a "humanized" or "human" antibody refers to an antibody in which the constant and variable framework region of one or more human immunoglobulins is fused with the binding region, e.g., the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; and Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, etc., or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., a, b, E and p for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institutes of Health, Bethesda, Md.).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "recombinant", when used with reference, e.g., to a cell, nucleic acid, protein, or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

As used herein, "T cells" refers to a sub-population of lymphocytes that mature in the thymus, and which display, among other molecules, T cell receptors on their surface. T cells can be identified by virtue of certain characteristics and biological properties, such as the expression of specific surface antigens including TCR, CD4 or CD8, optionally CD4 and IL-23R, the ability of certain T cells to kill tumor or infected cells, the ability of certain T cells to activate other cells of the immune system, and the ability to release protein molecules called cytokines that stimulate or inhibit the immune response. Any of these characteristics and activities can be used to identify T cells, using methods well-known in the art.

"Prominently expressed", when referring to an NKp46 polypeptide, means that the NKp46 polypeptide is expressed in a substantial number of tumor cells (e.g., PTCL cells, malignant or over-proliferating T or NK cells) taken from a given patient. While the definition of the term "prominently expressed" is not bound by a precise percentage value, in most cases a receptor said to be "prominently expressed" will be present on at least 30% or 40%, preferably 50%, 60%, 70%, 80%, or more, of the PTCL cells taken from a patient.

Within the context herein, the term "antibody that binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al., NCB/NLM/NIH, Bethesda, Md. 20894; Altschul et al., supra). The well-known Smith-Waterman algorithm may also be used to determine identity.

Production of Antibodies

"NKp46 polypeptide" and "NKp46 receptor" refer to a protein or polypeptide encoded by the Ncr1 gene or by a cDNA prepared from such a gene. Any naturally occurring isoform, allele or variant is encompassed by the term NKp46 polypeptide (e.g., an NKp46 polypeptide 90%, 95%, 98% or 99% identical to SEQ ID NO 1, or a contiguous sequence of at least 20, 30, 50, 100 or 200 amino acid residues thereof).

The 304 amino acid residue sequence of human NKp46 (isoform a) is shown as follows:

(SEQ ID NO: 1)
```
MSSTLPALLC VGLCLSQRIS AQQQTLPKPF IWAEPHFMVP

KEKQVTICCQ GNYGAVEYQL HFEGSLFAVD RPKPPERINK

VKFYIPDMNS RMAGQYSCIY RVGELWSEPS NLLDLVVTEM

YDTPTLSVHP GPEVISGEKV TFYCRLDTAT SMFLLLKEGR

SSHVQRGYGK VQAEFPLGPV TTAHRGTYRC FGSYNNHAWS

FPSEPVKLLV TGDIENTSLA PEDPTFPADT WGTYLLTTET

GLQKDHALWD HTAQNLLRMG LAFLVLVALV WFLVEDWLSR

KRTRERASRA STWEGRRRLN TQTL.
```

SEQ ID NO: 1 corresponds to NCBI accession number NP_004820, the disclosure of which is incorporated herein by reference. The human NKp46 mRNA sequence is described in NCBI accession number NM_004829, the disclosure of which is incorporated herein by reference.

Examples of antibodies that bind human NKp46 include, e.g., Bab281, mlgG1, available commercially from Beckman Coulter, Inc. (Brea, CA, USA) (see Pessino et al., J Exp Med, 1998, 188(5):953-960 and Sivori et al., Eur J Immunol, 1999, 29:1656-1666, describing chromium release cytotoxicity assays). Another NKp46 binding antibody is 9E2, mlgG1, available commercially from Becton Dickinson (Franklin Lakes, NJ, USA) and Miltenyi Biotec (Bergisch Gladback, Germany) (see Brando et al. (2005) J Leukoc Biol 78:359-371 and EI-Sherbiny et al. (2007) Cancer Research 67(18):8444-9). Another anti-NKp46 binding antibody is 195314, mlgG2b, available commercially from R&D Systems, Inc. (Minneapolis, USA) (see Nolte-'t Hoen et al. (2007) Blood 109:670-673). These antibodies all bind human NKp46, are of murine origin and have murine Fc domains. The antibodies all additionally inhibit the function of NKp46. The anti-NKp46 antibodies may include antibodies having variable region or CDR sequences from such Bab281, 9E2 or 195314 antibodies (e.g., where such heavy and/or light chain variable region is fused to a human constant region; a heavy chain variable region fused to a human IgG1 heavy chain constant region); alternatively, the anti-NKp46 antibodies may be an antibody other than the antibodies having variable region or CDR sequences from a Bab281, 9E2 or 195314 antibody.

In one aspect, an antibody is provided that competes with monoclonal antibody BAB281, 9E2 or 195314 and recognizes, binds to, or has immunospecificity for substantially or essentially the same, or the same, epitope or "epitopic site" on an NKp46 molecule as monoclonal antibody Bab281, 9E2 or 195314. In other embodiments, the monoclonal antibody consists of, or is a derivative or fragment of, antibody Bab281, 9E2 or 195314.

It will be appreciated that, while antibodies that bind to the same epitope as antibody Bab281, 9E2 or 195314 can be used, other antibodies can recognize and be raised against any part of the NKp46 polypeptide so long as the antibody causes the depletion of NKp46-expressing tumor cells or inhibits NKp46-expressing tumor cells' proliferation. For example, any fragment of NKp46, preferably but not exclusively human NKp46, or any combination of NKp46 fragments can be used as immunogens to raise antibodies, and the antibodies can recognize epitopes at any location within the NKp46 polypeptide, so long as they can do so on NKp46-expressing NK cells as described herein, e.g., and lead to the depletion of NKp46-expressing tumor cells. In an embodiment, the recognized epitopes are present on the cell surface, i.e., they are accessible to antibodies present outside of the cell. Most preferably, the epitope is the epitope specifically recognized by antibody Bab281, 9E2 or 195314. Further, antibodies recognizing distinct epitopes within NKp46 can be used in combination, e.g., to bind to NKp46 polypeptides with maximum efficacy and breadth among different individuals.

The antibodies may be produced by a variety of techniques known in the art. Typically, they are produced by immunization of a non-human animal, preferably a mouse, with an immunogen comprising an NKp46 polypeptide, preferably a human NKp46 polypeptide. The NKp46 polypeptide may comprise the full length sequence of a human NKp46 polypeptide, or a fragment or derivative thereof, typically an immunogenic fragment, i.e., a portion of the polypeptide comprising an epitope exposed on the surface of cells expressing an NKp46 polypeptide, preferably the epitope recognized by the Bab281, 9E2 or 195314 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human NKp46 polypeptide in a lipid membrane, typically at the surface of a cell. In a specific embodiment, the immunogen comprises intact cells, particularly intact human cells, optionally treated or lysed. In another embodiment, the polypeptide is a recombinant NKp46 polypeptide.

The step of immunizing a non-human mammal with an antigen may be carried out in any manner well-known in the art for stimulating the production of antibodies in a mouse (see, for example, E. Harlow and D. Lane, Antibodies: A Laboratory Manual., Cold Spring Harbor Laboratory Press, Cold Spring Harbor, NY (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well-known to those of skill in the art and are not limiting in any way. These parameters may be different for different immunogens, but are easily elucidated.

Similarly, the location and frequency of immunization sufficient to stimulate the production of antibodies is also well-known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with NKp46 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A. and X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, *Monoclonal Antibodies: Principles and Practice*, pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to NKp46 polypeptide gene products, optionally the epitope specifically recognized by antibody Bab281, 9E2 or 195314. The assay is typically a colorimetric ELISA-type assay, although any assay may be employed that can be adapted to the wells that the hybridomas are grown in. Other assays include radioimmunoassays or fluorescence-activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to NKp46 polypeptides, e.g., NKp46-expressing cells.

Hybridomas that are confirmed to produce a monoclonal antibody can be grown in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G Sepharose, or an anti-mouse Ig linked to a solid support such as agarose or Sepharose beads (all described, for example, in the Antibody Purification Handbook, Biosciences, Publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in Ward et al., Nature, 341 (1989), p. 544, the entire disclosure of which is herein incorporated by reference.

The identification of one or more antibodies that bind(s) to NKp46, particularly substantially or essentially the same epitope as monoclonal antibody Bab281, 9E2 or 195314, can be readily determined using any one of a variety of immunological screening assays in which antibody competition can be assessed. Many such assays are routinely practiced and are well-known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (Bab281, 9E2 or 195314, for example) and test antibodies are admixed (or pre-adsorbed) and applied to a sample containing NKp46 polypeptides. Protocols based upon Western blotting and the use of BIACORE analysis are suitable for use in such competition studies.

In certain embodiments, one pre-mixes the control antibodies (Bab281, 9E2 or 195314, for example) with varying amounts of the test antibodies (e.g., about 1:10 or about 1:100) for a period of time prior to applying to the NKp46 antigen sample. In other embodiments, the control and varying amounts of test antibodies can simply be admixed during exposure to the NKp46 antigen sample. As long as one can distinguish bound from free antibodies (e.g., by using separation or washing techniques to eliminate unbound antibodies) and Bab281, 9E2 or 195314 from the test antibodies (e.g., by using species-specific or isotype-specific secondary antibodies or by specifically labeling Bab281, 9E2 or 195314 with a detectable label), one can determine if the test antibodies reduce the binding of Bab281, 9E2 or 195314 to the antigens, indicating that the test antibody recognizes substantially the same epitope as Bab281, 9E2 or 195314. The binding of the (labeled) control antibodies in the absence of a completely irrelevant antibody can serve as the control high value. The control low value can be obtained by incubating the labeled (Bab281, 9E2 or 195314) antibodies with unlabeled antibodies of exactly the same type (Bab281, 9E2 or 195314), where competition would occur and reduce binding of the labeled antibodies. In a test assay, a significant reduction in labeled antibody reactivity in the presence of a test antibody is indicative of a test antibody that recognizes substantially the same epitope, i.e., one that "cross-reacts" or competes with the labeled (Bab281, 9E2 or 195314) antibody. Any test antibody that reduces the binding of Bab281, 9E2 or 195314 to NKp46 antigens by at least about 50%, such as at least about 60%, or more preferably at least about 80% or 90% (e.g., about 65-100%), at any ratio of Bab281, 9E2 or 195314:test antibody between about 1:10 and about 1:100 is considered to be an antibody that binds to substantially the same epitope or determinant as Bab281, 9E2 or 195314. Preferably, such test antibody will reduce the binding of Bab281, 9E2 or 195314 to the NKp46 antigen by at least about 90% (e.g., about 95%).

Competition can also be assessed by, for example, a flow cytometry test. In such a test, cells bearing a given NKp46 polypeptide can be incubated first with Bab281, 9E2 or 195314, for example, and then with the test antibody labeled with a fluorochrome or biotin. The antibody is said to compete with Bab281, 9E2 or 195314 if the binding obtained upon preincubation with a saturating amount of Bab281, 9E2 or 195314 is about 80%, preferably about 50%, about 40% or less (e.g., about 30%, 20% or 10%) of the binding (as measured by mean of fluorescence) obtained by the antibody without pre-incubation with Bab281, 9E2 or 195314. Alternatively, an antibody is said to compete with Bab281, 9E2 or 195314 if the binding obtained with a labeled Bab281, 9E2 or 195314 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which an NKp46 antigen is immobilized may also be employed. The surface in the simple competition assay is preferably a Biacore chip (or other media suitable for surface plasmon resonance analysis). The control antibody (e.g., Bab281, 9E2 or 195314) is then brought into contact with the surface at an NKp46-saturating concentration and the NKp46 and surface binding of the control antibody is measured. This binding of the control antibody is compared with the binding of the control antibody to the NKp46-containing surface in the absence of test antibody. In a test assay, a significant reduction in binding of the NKp46-containing surface by the control antibody in the presence of a test antibody indicates that the test antibody recognizes substantially the same epitope as the control antibody, such that the test antibody "cross-reacts" with the control antibody. Any test antibody that reduces the binding of control (such as Bab281, 9E2 or 195314) antibody to an NKp46 antigen by at least about 30% or more, preferably about 40%, can be considered to be an antibody that binds to substantially the same epitope or determinant as a control (e.g., Bab281, 9E2 or 195314). Preferably, such a test antibody will reduce the binding of the control antibody (e.g., Bab281, 9E2 or 195314) to the NKp46 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the NKp46 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/characterization methods, an epitope region for an anti-NKp46 antibody may be determined by epitope "footprinting" using chemical modification of the exposed amines/carboxyls in the NKp46 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring, H., Analytical Biochemistry, 267(2): 252-259 (1999) and Engen, J. R. and Smith, D. L. Anal. Chem. 73:256A-265A (2001). Another example of a suitable epitope identification technique is nuclear magnetic resonance epitope mapping (NMR), where typically the position of the signals in two-dimensional NMR spectra of the free antigen and the antigen complexed with the antigen-binding peptide, such as an antibody, are compared. The antigen typically is selectively isotopically labeled with 15N so that only signals corresponding to the antigen and no signals from the antigen-binding peptide are seen in the NMR spectrum. Antigen signals originating from amino acids involved in the interaction with the antigen-binding peptide typically will shift position in the spectrum of the complex compared to the spectrum of the free antigen, and the amino acids involved in the binding can be identified that way. See, e.g., Ernst Schering Res Found Workshop, 2004, (44):149-67; Huang et al., Journal of Molecular Biology, 281(1):61-67 (1998); and Saito and Patterson, Methods, 1996 Jun., 9(3):516-24.

Epitope mapping/characterization also can be performed using mass spectrometry methods. See, e.g., Downard, J. Mass. Spectrom., 2000 April, 35(4):493-503 and Kiselar and Downard, Anal. Chem., 1999 May 1, 71(9):1792-801. Protease digestion techniques also can be useful in the context of epitope mapping and identification. Antigenic determinant-relevant regions/sequences can be determined by protease digestion, e.g., by using trypsin in a ratio of about 1:50 to NKp46 or overnight digestion at pH 7-8, followed by mass spectrometry (MS) analysis for peptide identification. The peptides protected from trypsin cleavage by the anti-NKp46 binder can subsequently be identified by comparison of samples subjected to trypsin digestion and samples incubated with antibody and then subjected to digestion by, e.g., trypsin (thereby revealing a footprint for the binder). Other enzymes like chymotrypsin, pepsin, etc. also or alternatively can be used in similar epitope characterization methods. Moreover, enzymatic digestion can provide a quick method for analyzing whether a potential antigenic determinant sequence is within a region of the NKp46 polypeptide that is not surface exposed and, accordingly, most likely not relevant in terms of immunogenicity/antigenicity. See, e.g., Manca, Ann Ist Super Sanita, 1991, 27:15-9 for a discussion of similar techniques.

Site-directed mutagenesis is another technique useful for elucidation of a binding epitope. For example, in "alanine scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence the overall fold of the protein. See, e.g., Clackson and Wells, Science, 1995, 267:383-386 and Wells, Proc Natl Acad Sci USA, 1996, 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, Biacore) and reflectometric interference spectroscopy (RIfS). See, e.g., Fagerstam et al., Journal of Molecular Recognition, 1990, 3:208-14; Nice et al., J. Chromatogr., 1993, 646:159-168; Leipert et al., Angew. Chem. Int. Ed., 1998, 37:3308-3311; and Kroger et al., Biosensors and Bioelectronics, 2002, 17:937-944.

It should also be noted that an antibody binding the same or substantially the same epitope as an antibody can be identified in one or more of the exemplary competition assays described herein.

Once antibodies are identified that are capable of binding NKp46 and/or having other desired properties, they will also typically be assessed, using standard methods including those described herein, for their ability to bind to other polypeptides, including unrelated polypeptides. Ideally, the antibodies only bind with substantial affinity to NKp46, e.g., human NKp46, and do not bind at a significant level to unrelated polypeptides. However, it will be appreciated that, as long as the affinity for NKp46 is substantially greater (e.g., 5×, 10×, 50×, 100×, 500×, 1000×, 10,000×, or more) than it is for other, unrelated polypeptides), then the antibodies are suitable for use in the present methods.

The binding of the antibodies to NKp46-expressing cells can also be assessed in non-human primates, e.g., cynomolgus monkeys, or other mammals such as mice. The disclosure therefore provides an antibody, as well as fragments and derivatives thereof, wherein said antibody, fragment or derivative specifically binds NKp46, and which furthermore binds NKp46 from non-human primates, e.g., cynomolgus monkeys.

Upon immunization and production of antibodies in a vertebrate or cell, particular selection steps may be performed to isolate antibodies as claimed. In this regard, the disclosure also relates to methods of producing such antibodies, comprising: (a) immunizing a non-human mammal with an immunogen comprising an NKp46 polypeptide; (b) preparing antibodies from said immunized animal; and (c) selecting antibodies from step (b) that are capable of binding NKp46.

In one aspect of any of the embodiments, the antibodies prepared according to the present methods are monoclonal antibodies. In another aspect, the non-human animal used to produce antibodies according to the methods herein is a mammal, such as a rodent, bovine, porcine, fowl, horse, rabbit, goat, or sheep.

According to an alternate embodiment, the DNA encoding an antibody that binds an epitope present on NKp46 polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies, e.g., antibody Bab281, 9E2 or 195314, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or modifying the sequence of the antibody, e.g., in the antigen-binding site in order to optimize the binding specificity of the antibody.

Recombinant expression in bacteria of DNA encoding the antibody is well-known in the art (see, for example, Skerra et al., Curr. Opinion in Immunol., 5:256 (1993) and Pluckthun, Immunol. 130:151 (1992).

Once an antigen-binding compound is obtained it may be assessed for its ability to induce ADCC or CDC towards, inhibit the activity and/or proliferation of and/or cause the elimination of NKp46-expressing target cells. Assessing the antigen-binding compound's ability to induce ADCC or CDC (complement-dependent cytotoxicity) or generally lead to the elimination or inhibition of activity of NKp46-expressing target cells can be carried out at any suitable stage of the method. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human-suitable (e.g., made chimeric or humanized in the case of an antibody), where a cell expressing the antigen-binding compound (e.g., a host cell expressing a recombinant antigen-binding compound) has been obtained and is assessed for its ability to produce functional antibodies (or other compounds), and/or where a quantity of antigen-binding compound has been produced and is to be assessed for activity (e.g., to test batches or lots of product). Generally the antigen-binding compound will be known to specifically bind to an NKp46 polypeptide. The step may involve testing a plurality (e.g., a very large number using high-throughput screening methods or a smaller number) of antigen-binding compounds.

Testing CDC and ADCC can be carried out can be determined by various assays including those known in the art and those described in the experimental examples herein. Testing ADCC typically involves assessing cell-mediated cytotoxicity in which an NKp46-expressing target cell (e.g., a PTCL cell or other NKp46-expressing cell) with bound anti-NKp46 antibody is recognized by an effector cell bearing Fc receptors, without the involvement of complement. A cell which does not express an NKp46 antigen can optionally be used as a control. Activation of NK cell cytotoxicity is assessed by measuring an increase in cytokine production (e.g., IFN-γ production) or cytotoxicity markers (e.g., CD107 mobilization). Preferably the antibody will induce an increase in cytokine production, expression of cytotoxicity markers, or target cell lysis of at least 20%, 50%, 80%, 100%, 200% or 500% in the presence of target cells, compared to a control antibody (e.g., an antibody not binding to NKp46, an NKp46 antibody having murine constant regions). In another example, lysis of target cells is detected, e.g., in a chromium release assay; preferably the antibody will induce lysis of at least 10%, 20%, 30%, 40% or 50% of target cells.

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen-binding site or variable region. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules, (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Included, inter alia, are a nanobody, domain antibody, single domain antibody or "dAb".

In certain embodiments, the DNA of a hybridoma producing an antibody can be modified prior to insertion into an expression vector, for example, by substituting the coding sequence for human heavy- and light-chain constant domains in place of the homologous non-human sequences (e.g., Morrison et al., PNAS, p. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Thus, according to another embodiment, the antibody is humanized. "Humanized" forms of antibodies are specific chimeric immunoglobulins, immunoglobulin chains or fragments thereof (such as Fv, Fab, Fab', F(ab')2, or other antigen-binding subsequences of antibodies) which contain a minimal sequence derived from the murine immunoglobulin. For the most part, humanized antibodies are human immunoglobulins (recipient antibody) in which residues from a complementarity-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321: p. 522 (1986); Reichmann et al., Nature, 332: p. 323 (1988); Presta, Curr. Op. Struct. Biol., 2: p. 593 (1992); Verhoeyen et al., Science, 239: p. 1534; and U.S. Pat. No. 4,816,567, the entire disclosures of which are herein incorporated by reference.) Methods for humanizing the antibodies are well-known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol., 151: p. 2296 (1993); Chothia and Lesk, J. Mol. Biol., 196: p. 901 (1987)). Another method uses a particular framework from the consensus sequence of all human antibodies of a particular subgroup of light or heavy chains. The same framework can be used for several different humanized antibodies (Carter et al., PNAS, 89: p. 4285 (1992); Presta et al., J. Immunol., 151: p. 2623 (1993)).

It is further important that antibodies be humanized with retention of high affinity for NKp46 receptors and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host that has had its immunoglobulin genes replaced by functional human immunoglobulin genes. Thus, antibodies produced by this mouse or in hybridomas made from the B cells of this mouse are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362:255 (1993)), or by selection of antibody repertoires using phage display methods. Such techniques are known to the skilled person and can be implemented starting from monoclonal antibodies as disclosed in the present application.

In one embodiment, an NKp46 binding compound is provided, preferably an anti-NKp46 antibody, further bound to a second moiety, wherein the antibody is capable of delivering the second moiety to an NKp46-expressing cell. Optionally the second moiety is a therapeutic agent or a toxic agent (e.g., in the treatment methods where the NKp46 binding compound is intended for administration to an individual), and/or a detectable agent (e.g., when the NKp46 binding compound is intended for use in a detection step).

While antibodies in underivatized or unmodified form, particularly of the IgG1 or IgG3 type, can be cytotoxic towards overproliferating cells such as those from a PTCL patient, e.g., by directing ADCC and/or CDC toward NKp46-expressing PTCL cells, it is also possible to prepare derivatized antibody immunoconjugates that are cytotoxic. In one embodiment, once the NKp46-specific antibodies are isolated and optionally otherwise modified (e.g., humanized), they will be derivatized to make them toxic to cells. In this way, administration of the antibody to PTCL patients will lead to the relatively specific binding of the antibody to overproliferating cells, thereby directly killing or inhibiting the cells underlying the disorder.

Any of a large number of toxic moieties or strategies can be used to produce such antibodies. In certain embodiments, the antibodies will be directly derivatized with radioisotopes or other toxic compounds. Examples of toxic agents used in immunoconjugates in development include, in particular, taxanes, anthracyclines, camptothecins, epothilones, myto-mycins, combretastatins, vinca alkaloids, nitrogen mustards, maytansinoids, calicheamycins, duocarmycins, tubulysins, dolastatins and auristatins, enediynes, pyrrolobenzodiaz-epines, ethylenimines, radioisotopes, therapeutic proteins and peptides, and toxins or fragments thereof. Any type of moiety with a cytotoxic or cytoinhibitory effect can be used in conjunction with the present antibodies to inhibit or kill specific NK receptor-expressing cells, including radioisotopes, toxic proteins, and toxic small molecules, such as drugs, toxins, immunomodulators, hormones, hormone antagonists, enzymes, oligonucleotides, enzyme inhibitors, therapeutic radionuclides, angiogenesis inhibitors, chemotherapeutic drugs, vinca alkaloids, epidophyllotoxins, antimetabolites, alkylating agents, antibiotics, antimitotics, and antiangiogenic and apoptotoic agents, particularly doxorubicin, methotrexate, camptothecans, nitrogen mustards, gemcitabine, alkyl sulfonates, nitrosoureas, triazenes, folic acid analogs, pyrimidine analogs, purine analogs, platinum coordination complexes, Pseudomonas exotoxin, ricin, 5-fluorouridine, ribonuclease (RNase), DNase I, Staphylococcal enterotoxin-A, pokeweed antiviral protein, gelonin, diphtherin toxin, Pseudomonas exotoxin, Pseudomonas endotoxin and others (see, e.g., Remington's Pharmaceutical Sciences, 19th Ed. (Mack Publishing Co. 1995); Goodman and Gilman's The Pharmacological Basis of Therapeutics (McGraw-Hill, 2001); Pastan et al. (1986) Cell 47:641; Goldenberg (1994) Cancer Journal for Clinicians 44:43; and U.S. Pat. No. 6,077,499, the entire disclosures of which are herein incorporated by reference).

In one embodiment, the antibody will be derivatized with a radioactive isotope. Any of a number of suitable radioactive isotopes can be used, including, but not limited to, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-ill, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-105, Palladium-109, Praseodymium-143, Promethium-149, Erbium-169, Iridium-194, Gold-198, Gold-199, and Lead-211. In general, the radionuclide preferably has a decay energy in the range of 20 to 6,000 keV, preferably in the ranges of 60 to 200 keV for an Auger emitter, 100-2,500 keV for a beta emitter, and 4,000-6,000 keV for an alpha emitter. Also envisaged are radionuclides that substantially decay with generation of alpha-particles.

In view of the ability of the anti-NKp46 antibodies to induce ADCC and CDC, the antibodies can also be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g., substitutions, deletions, insertions), and/or altered types of glycosylation, e.g., hypofucosylation. Such modifications can affect interaction with Fc receptors: FcγRI (CD64), FcγRII (CD32), and FcγRII (CD 16). FcγRI (CD64), FcγRIIA (CD32A) and FcγRII (CD 16) are activating (i.e., immune system-enhancing) receptors while FcγRIIB (CD32B) is an inhibiting (i.e., immune system-dampening) receptor. A modification may, for example, increase binding of the Fc domain to FcγRIIa on effector (e.g., NK) cells.

Anti-NKp46 antibodies preferably comprise an Fc domain (or portion thereof) of human IgG1 or IgG3 isotype, optionally modified. Residues 230-341 (Kabat EU) are the Fc CH2 region. Residues 342-447 (Kabat EU) are the Fc CH3 region. Anti-NKp46 antibodies may comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody except for the one or more amino acid modifications in the Fc region). For example, one or both of the histidine residues at amino acid positions 310 and 435 may be substituted, for example by lysine, alanine, glycine, valine, leucine, isoleucine, proline, methionine, tryptophan, phenylalanine, serine or threonine (see, e.g., PCT Publication No. WO 2007/080277); such substituted constant regions provide decreased binding to the inhibitory FcγRIIB without decreasing binding to the activatory FcγRIIIA. In some embodiments, such modifications increase the affinity of the variant Fc region for FcγRIIIA and/or FcγRIIA and also enhance the affinity of the variant Fc region for FcγRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells.

The affinities and binding properties of the anti-NKp46 antibodies for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, and immunoprecipitation assays.

In some embodiments, anti-NKp46 antibodies comprising a variant Fc region comprise at least one amino acid modification (for example, possessing 1, 2, 3, 4, 5, 6, 7, 8, 9, or more amino acid modifications) in the CH3 domain of the Fc region. In other embodiments, anti-NKp46 antibodies comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, anti-NKp46 antibodies comprise at least two amino acid modifications (for example, possessing 2, 3, 4, 5, 6, 7, 8, 9, or more amino acid modifications), wherein at least one such modification is in the CH3 region and at least one such modification is in the CH2 region. Further encompassed are amino acid modifications in the hinge region. In a particular embodiment, amino acid modifications in the CH1 domain of the Fc region, which is defined as extending from amino acids 216-230, are encompassed.

Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604.

Anti-NKp46 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439.

Anti-NKp46 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g., S239D, S298A, A330L, I332E, E333A and/or K334A substitutions). In one example, the residues at amino acid positions S239 and I332 may be substituted, for example by another amino acid, optionally wherein the S239 modification is an S239D substitution and the I332 modification is an I332E substitution; such substituted constant regions provide increased binding to the activatory FcγRIIIA.

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) J. Biol. Chem. 277:26733-26740 and Umana et al. (1999) Nat. Biotech. 17:176-1, as well as European Patent No. EP 1,176,195 and PCT Publications WO 06/133148, WO 03/035835, and WO 99/54342, each of which is incorporated herein by reference in its entirety.

Generally, such antibodies with altered glycosylation are "glyco-optimized" such that the antibody has a particular N-glycan structure that produces certain desirable properties, including, but not limited to, enhanced ADCC and effector cell receptor binding activity when compared to non-modified antibodies or antibodies having a naturally occurring constant region and produced by murine myeloma NSO and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennary structures with very low or no bisecting N-acetylglucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trends Biotechnol. 15:26-31 (1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

Non-fucosylated oligosaccharide structures (at Asn297) have recently been associated with dramatically increased in vitro ADCC activity. "Asn 297" means amino acid asparagine located at about position 297 in the Fc region; based on minor sequence variations of antibodies, Asn297 can also be located some amino acids (usually not more than +3 amino acids) upstream or downstream.

Historically, antibodies produced in CHO cells contain about 2 to 6% in the population that are nonfucosylated. YB2/0 (rat myeloma) and Lec13 cell line (a lectin mutant of the CHO line which has a deficient GDP-mannose 4,6-dehydratase leading to the deficiency of GDP-fucose or GDP sugar intermediates that are the substrate of alpha6-fucosyltransferase) have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

Anti-NKp46 antibodies may be glycosylated with a sugar chain at Asn297, said antibody showing increased binding affinity via its Fc portion to FcγRII. In one embodiment, an antibody will comprise a constant region comprising at least one amino acid alteration in the Fc region that improves antibody binding to FcγRIIIa and/or ADCC.

In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g., complex, hybrid and high-mannose structures) which lacks fucose. In one embodiment, an antibody composition is free of antibodies comprising a core carbohydrate structure having fucose. The core carbohydrate will preferably be a sugar chain at Asn297.

In one embodiment an antibody composition, e.g., a composition comprising antibodies which bind to NKp46, is glycosylated with a sugar chain at Asn297, wherein the antibodies are partially fucosylated. Partially fucosylated antibodies are characterized in that the proportion of anti-NKp46 antibodies in the composition that lack fucose within the sugar chain at Asn297 is between 20% and 90%, preferably between 20% and 80%, preferably between 20% and 50%, 55%, 60%, 70% or 75%, between 35% and 50%, 55%, 60%, 70% or 75%, or between 45% and 50%, 55%, 60%, 70% or 75%. Preferably the antibody is of human IgG1 or IgG3 type.

The sugar chain can further show any characteristics (e.g., presence and proportion of complex, hybrid and high-mannose structures), including the characteristics of N-linked glycans attached to Asn297 of an antibody from a human cell, or of an antibody recombinantly expressed in a rodent cell, murine cell (e.g., CHO cell) or avian cell.

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22, the disclosures of which are incorporated herein by reference). Other examples have included use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotein-modifying glycosyl transferases (e.g., beta(1,4)-N-acetylglucosaminyl-transferase III (GnTHI)) such that antibodies expressed in the engineered cell lines exhibit increased bisecting GlcNac structures which results in increased ADCC activity of the antibodies (PCT Publication WO 99/54342 by Umana et al. and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino et al. (1975) Biochem. 14:5516-5523). In other examples, a cell line producing an antibody can be treated with a glycosylation inhibitor; Zhou et al. (Biotech. and Bioengin. 99: 652-665 (2008)) described treatment of CHO cells with the alpha-mannosidase I inhibitor kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Other example of cell lines include a variant CHO cell line, Led 3 cells, with reduced ability to attach fucosyl to Asn(297)-linked carbohydrates, also resulting in hypofucosylation of antibodies expressed in that host cell (WO 2003/035835 (Presta et al) and Shields, R. L. et al. (2002) J. Biol. Chem. 277:26733-26740, the disclosures of which are incorporated herein by reference). In another embodiment, the antibody is expressed in an avian cell, preferably an EBx® cell (Vivalis, France) which naturally yields antibodies with low fucose content, e.g., WO 2008/142124. Hypofucosylated glycans can also be produced in cell lines of plant origin, e.g., WO 2007/084926 (Biolex Inc.) and WO 2008/006554 (Greenovation Biotech GMBH), the disclosures of which are incorporated herein by reference.

Antibody Formulations

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The antibodies may be employed in a method of eliminating, inhibiting or depleting, the activity of NKp46-expressing PTCL cells in a patient. This method comprises the step of administering said composition to said patient. Such method will be useful for both prophylaxis and therapeutic purposes.

For use in administration to a patient, the composition will be formulated for administration to the patient. The compositions may be administered orally, parenterally, by inhalation spray, topically, rectally, nasally, buccally, vaginally or via an implanted reservoir. The techniques used herein include subcutaneous, intravenous, intramuscular, intra-articular, intra-synovial, intrasternal, intrathecal, intrahepatic, intralesional and intracranial injection or infusion techniques.

Sterile injectable forms of the compositions may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms, including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

Several monoclonal antibodies have been shown to be efficient in clinical situations, such as Rituxan™ (Rituximab), Herceptin™ (Trastuzumab) or Xolair™ (Omalizumab), and similar administration regimens (i.e., formulations and/or doses and/or administration protocols) may be used with the antibodies that bind NKp46. For example, an antibody present in a pharmaceutical composition can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition for injection (e.g., intramuscular, i.v.) could be prepared to contain sterile buffered water (e.g., 1 ml for intramuscular), and between about 1 ng to about 100 mg, e.g., about 50 ng to about 30 mg or, more preferably, about 5 mg to about 25 mg, of an anti-NKp46 antibody.

According to another embodiment, the antibody compositions may further comprise another therapeutic agent, including agents normally utilized for the particular therapeutic purpose for which the antibody is being administered, notably for the treatment of a PTCL. The additional therapeutic agent will normally be present in the composition in amounts typically used for that agent in a monotherapy for the particular disease or condition being treated. Such therapeutic agents include, but are not limited to, anti-inflammation agents, steroids, immune system suppressors, antibiotics, antivirals and other antibodies and fragments thereof.

Diagnosis and Treatment of Malignancies

Methods useful in the diagnosis, prognosis and monitoring of a peripheral T-cell lymphoma in an individual are described. In one embodiment, the methods comprise determining the level of expression of an NKp46 nucleic acid or polypeptide in a biological sample from a patient, e.g., in tumor cells found in a biological sample (e.g., a biopsy). In one embodiment, the methods comprise determining the level of expression of an NKp46 nucleic acid or polypeptide in a biological sample and comparing the level to a reference level (e.g., a value, weak cell surface staining, etc.) corresponding to a healthy individual. A determination that a biological sample expresses an NKp46 nucleic acid or polypeptide at a level that is increased compared to the reference level indicates that the patient has a peripheral T-cell lymphoma, e.g., an NKp46-positive peripheral T-cell lymphoma. Optionally, detecting an NKp46 polypeptide in a biological sample comprises detecting the NKp46 polypeptide expressed on the surface of a lymphocyte.

In one embodiment, the methods comprise: (a) determining whether an individual has a peripheral T-cell lymphoma; and (b) if the individual has a peripheral T-cell lymphoma, determining whether the individual has peripheral T-cell lymphoma cells that express an NKp46 polypeptide.

Also provided is a method for the assessment of the development level of a PTCL (staging disease) permitting the evaluation of the proportion (e.g., percentage) of malignant PTCL cells present within a certain body compartment of a patient. According to this method, cells from a biological sample collected from said body compartment are brought into contact with an anti-NKp46 antibody and tumor (PTCL) cells (e.g., the proportion of cells) expressing an NKp46 polypeptide at their surface is measured. The cells may be, for example, CD4+ cells or CD4-CD8+ cells. A finding that tumor cells express NKp46, e.g., predominantly express NKp46, may be used to indicate that the PTCL is an aggressive or advanced PTCL (e.g., stage IV, or more generally beyond stage II).

Also provided is a method for PTCL diagnosis, comprising bringing cells from a biological sample from an individual into contact with an anti-NKp46 antibody and measuring the proportion (e.g., percentage) of T cells expressing an NKp46 polypeptide at their surface, and comparing such proportion to the average proportion (e.g., percentage) of T cells expressing an NKp46 polypeptide at their surface observed in non-PTCL humans (preferably in healthy humans), wherein a PTCL-positive diagnosis is made when said measured proportion is significantly higher than said average proportion.

Also provided are therapeutic methods for treating individuals having a PTCL, susceptible to a PTCL or having experienced a PTCL, wherein the treatment involves administering anti-NKp46 antibodies, anti-NKp46 antibody compositions, and/or related compositions to an individual having or susceptible to PTCL. In one embodiment, the PTCL is an aggressive or advanced PTCL (e.g., stage IV, or more generally beyond stage II). In one embodiment, the PTCL is a non-cutaneous PTCL. In one embodiment, the PTCL is an aggressive T-cell lymphoma. In one embodiment, the patient has relapsing or refractory disease. In one embodiment, the patient has a poor prognosis for disease progression (e.g., poor prognosis for survival) or has a poor prognosis for response to a therapy.

In one embodiment, the PTCL is an aggressive T-cell neoplasm. In one embodiment, the PTCL is an aggressive T-cell neoplasm. In one embodiment, the PTCL is an aggressive non-cutaneous PTCL. In one embodiment, the PTCL is an aggressive cutaneous PTCL, optionally a primary cutaneous CD4+ small/medium T-cell lymphoma or a primary CD8+ small/medium T-cell lymphoma. PTCL and PTCL-NOS as used herein exclude the cutaneous T-cell lymphomas Sezary Syndrome and mycosis fungoides, which are considered distinct pathologies.

In one embodiment, the PTCL is a nodal (e.g., primarily or predominantly nodal) PTCL. Predominantly nodal PTCLs include PTCL-NOS (Peripheral T-cell lymphomas, not otherwise specified), anaplastic large cell lymphomas (ALCL) and angioimmunoblastic T-cell lymphomas (AITL). For example a PTCL may be an aggressive, non-cutaneous, predominantly nodal PCTL (the disease may additionally have extra-nodal presentation).

In one embodiment, the PTCL is an extranodal (e.g., primarily extranodal) PTCL. For example a PTCL may be an aggressive, non-cutaneous, extranodal PCTL.

In one embodiment, the PTCL is an adult T-cell leukemia or lymphoma (ATL), e.g., an HTLV+ ATL.

In one embodiment, the PTCL is an orthovisceral extranodal PTCL. In one embodiment, the PTCL is an extranodal NK−/T-cell lymphoma, nasal type. In one embodiment, the PTCL is an enteropathy-associated T-cell lymphoma.

In one embodiment, the PTCL is an anaplastic large cell lymphoma (ALCL), optionally an ALK+ ALCL, optionally an ALK− ALCL. ALK+ ALCL generally enjoys favorable prognostics using conventional therapy (93% 5-year survival) but ALK− ALCL has poor prognostics (37%). ALCL is generally characterized by uniform CD30 surface expression. Anti-NKp46 antibodies can therefore be used in combination with anti-CD30 antibodies (e.g., Adcetris™ (brentuximab vedotin, Seattle Genetics, Inc.)), for the treatment of ALCL. ALCL is generally also CD4+, although with occasional CD4-CD8+ cases. Anti-NKp46 antibodies can therefore be used in combination with anti-CD4 antibodies to treat ALCL.

In one embodiment, the PTCL is an angioimmunoblastic T-cell lymphoma (AITL), optionally a cutaneous AITL, optionally a primary cutaneous CD4+ small/medium T-cell lymphoma or a primary CD8+ small/medium T-cell lymphoma, optionally a non-cutaneous AITL.

In one embodiment, the PTCL is an intestinal lymphoma, e.g., an intestinal ALCL.

In one embodiment, the PTCL is a T-cell prolymphocytic leukemia.

In one embodiment, a PTCL is a PTCL-NOS (Peripheral T-cell lymphoma, not otherwise specified). PTCL-NOS, also referred to as PCTL-U or PTCL-unspecified, are aggressive lymphomas, mainly of nodal type, but extranodal involvement is common. The majority of nodal cases are CD4+ and CD8-, and CD30 can be expressed in large cell variants. Most patients with PTCL-NOS present with nodal involvement; however, a number of extranodal sites may also be involved (e.g., liver, bone marrow, gastrointestinal, skin). Studies generally report a 5-year overall survival of approximately 30%-35% using standard chemotherapy. In the past, a number of definite entities corresponding to recognizable subtypes of T-cell neoplasm, such as Lennert lymphoma, T-zone lymphoma, pleomorphic T-cell lymphoma, small and medium-sized and large-cell T-cell lymphoma, and T-immunoblastic lymphoma have been described, but evidence that these correspond to distinctive clinicopathological entities is still lacking. For this reason the recent World Health Organization (WHO) classification of the hematopoietic and lymphoid neoplasms has collected these under the single broad category of PTCL-NOS/U. PTCL-NOS may therefore be specified to exclude certain distinctive clinicopathological entities such as T-cell prolymphocytic leukemia, aggressive NK-cell leukemia, ATL/adult T-cell leukemia, extranodal NK−/T-cell leukemia nasal type, EATL/enteropathy-type T-cell lymphoma, hepatosplenic T-cell lymphoma, subcutaneous panniculitis-like T-cell lymphoma, ALCL/anaplastic large-cell lymphoma, and/or AITL/angioimmunoblastic T-cell lymphoma. Anti-NKp46 antibodies can therefore be used in combination with anti-CD4 antibodies to treat PTCL-NOS. Anti-NKp46 antibodies can therefore be used in combination with anti-CD30 antibodies to treat PTCL-NOS that are CD30+.

PTCL diagnosis criteria can be those of standard medical guidelines, for example, according to the World Health Organization (WHO) classification system (see, e.g., World Health Organization, WHO Classification of Tumours of Haematopoietic and Lymphoid Tissues, $4^{th}$ ed. Lyon, France: IARC Press, 2008). See also, e.g., Foss et al. (2011) Blood 117:6756-6767, the disclosures of which are incorporated herein by reference.

In one exemplary aspect, a method is provided of reducing progression of PTCL in a mammalian host, (e.g., a human patient) having a detectable level of cancer cells, comprising administering an anti-NKp46 antibody, an anti-NKp46 antibody composition, or a related composition (e.g., a nucleic acid encoding an anti-NKp46 antibody) in an amount sufficient to detectably reduce the progression of the hematological malignancies in the host.

In one exemplary aspect, a method is provided of treating PTCL in an individual having a poor disease prognosis and/or who has relapsed, is resistant or is not responsive to therapy with a first therapeutic agent.

Disease or cancer diagnosis and progression can be defined by standard criteria for the particular type of disease. PTCL (e.g., PTCL-NOS) is typically based on examination of peripheral blood or tissue biopsy for histological features supplemented by detailed immunohistochemistry, flow cytometry, cytogenetics and molecular genetics. Examination may include, for example, full blood count and differential tests of renal and hepatic function, lactate dehydrogenase (LDH), Beta2 microglobulin, albumin, serum calcium, uric acid, bone marrow biopsy, chest X-ray and computerized tomography (CT) scan of chest, abdomen and pelvis. Progression is optionally determined by assessing the selective clonal expansion of initiated cells. Methods for detecting cancers and cancer progression can be achieved by any suitable technique, several examples of which are known in the art. Examples of suitable techniques include PCR and RT-PCR (e.g., of cancer cell-associated genes or "markers"), biopsy, imaging techniques, karyotyping and other chromosomal analysis, immunoassay/immunocytochemical detection techniques, histological and/or histopathology assays, cell kinetic studies and cell cycle analysis, flow cytometry, and physical examination techniques (e.g., for physical symptoms).

In one embodiment, diagnosing or assessing PTCL (e.g., PTCL-NOS) comprises chromosomal analysis. Cases of PTCL-NOS often show heterogeneous, variable morphology, with losses having been reported in 3q, 6q, 9p, 10q, 12q and/or 5q, and recurrent chromosomal gains, including in 8q, 9p and/or 19q. One CGH study in PTCL-NOS has shown frequent gains of 7q22-31, 1q, 3p, 5p and 8q24qter and losses of 6q22-24 and 10p13pter and cases with complex karyotypes had poor disease prognosis.

In one embodiment, diagnosing or assessing PTCL comprises biomarker analysis. In one embodiment, a patient having a poor disease prognosis is identified by biomarker analysis wherein the presence or absence (e.g., level of) a nucleic acid or protein is detected in a biological sample from the patient (e.g., in tumor cells from a patient). A range of biomarkers are known in PTCL, including, e.g., p53, Ki-67, BCL-2, BCL-XL, CD26, EBV, MDR, CCND2, CCR4, NK-Kb, CCR3, CXCR3, PRDM1, and ALK-1.

In one embodiment, diagnosing or assessing PTCL comprises detecting chemokine receptors CXCR3 and/or CCR4 (e.g., detecting the presence or absence of CXCR3 and/or CCR4 nucleic acid or proteins, or levels of CXCR3 and/or CCR4 nucleic acid or proteins). CXCR3 and CCR4 have been found respectively in 63% and 34% of PTCL-NOS (Percy et al., Int. Class Diseases for Oncol. (ICD-O-3), $3^{rd}$ ed. Geneva, Switzerland: World Health Organization (2000)). In one embodiment, a determination that a patient has a PTCL (e.g., PTCL cells) that is CXCR3-positive and CCR4-negative indicates that the patient has a poor disease prognosis.

In one embodiment, enteropathy-type T-cell lymphoma is diagnosed and/or treated with an anti-NKp46 antibody composition. Enteropathy-associated T-cell lymphoma (EATL) is considered a complication of celiac disease (CD); see, e.g., Di Sabatino et al. (2012) Blood 119:2458-2468. This tumor derives from the neoplastic transformation of aberrant intraepithelial T lymphocytes emerging in celiac patients unresponsive to a gluten-free diet. Poor adherence to a gluten-free diet, HLA-DQ2 homozygosity, and late diagnosis of CD are recognized as risk factors for malignant evolution of CD. Refractory CD (RCD) often progresses to EATL. Diagnosing or assessing EATL may thus comprise detecting a marker of EATL, or of CD or RCD that is susceptible to progressing to EATL, or identifying a patient as having EATL, or CD or RCD susceptible to progressing to EATL. In one embodiment, enteropathy-type T-cell lymphoma is treated with (by administering) an anti-NKp46 antibody composition, in combination with a second therapeutic agent used in the treatment of EATL, e.g., a chemotherapy, e.g., CHOP comprising cyclophosphamide, doxorubicin, vincristine, prednisone, or other multi-chemotherapeutic agent regimens.

Delivering anti-NKp46 antibodies to a subject (either by direct administration or expression from a nucleic acid therein, such as from a pox viral gene transfer vector comprising anti-NKp46 antibody-encoding nucleic acid sequence(s)) and practicing the other methods herein can be used to reduce, treat, prevent, or otherwise ameliorate any suitable aspect of cancer progression (notably PTCL progression). The methods can be particularly useful in the reduction and/or amelioration of tumor growth (e.g., percentage (tumor cells compared to healthy T cells), number of tumor cells in circulation), and any parameter or symptom associated therewith (e.g., biomarkers). Methods that reduce, prevent, or otherwise ameliorate such aspects of cancer progression, independently and collectively, are advantageous features.

In another aspect, a method is provided of reducing the risk of cancer progression, reducing the risk of further cancer progression in a cell population that has undergone initiation, and/or providing a therapeutic regimen for reducing cancer progression in a human patient, which comprises administering to the patient one or more first treatments (e.g., induction therapy, such as a chemotherapeutic agent or an antibody) in an amount and regimen sufficient to achieve a response (partial or complete response), and then administering an amount of an anti-NKp46 antibody or related composition (or applying a combination administration method) to the patient.

In a further aspect, a method is provided of promoting remission of a PTCL in a mammalian host, such as a human patient, comprising administering a composition comprising an anti-NKp46 antibody to the host, so as to promote PTCL remission in the host.

In an even further aspect, a method is provided for reducing the risk of developing a PTCL, reducing the time to onset of a cancerous condition, and/or reducing the severity of a PTCL diagnosed in the early stages, comprising administering to a host a prophylactically effective amount of an anti-NKp46 antibody or related composition so as to achieve the desired physiological effect(s).

In a further aspect, a method is provided of increasing the likelihood of survival over a relevant period in a human patient diagnosed with PTCL. In another aspect, a method is provided for improving the quality of life of a PTCL patient, comprising administering to the patient a composition in an amount effective to improve the quality of life thereof. In a further aspect, methods described herein can be applied to significantly reduce the number of PTCL cells in a vertebrate host, such that, for example, the total number of PTCL cells is reduced. In a related sense, a method is provided for killing (e.g., either directly or indirectly causing the death of) PTCL cells in a vertebrate, such as a human cancer patient.

According to another embodiment, the antibody compositions may be used in combined treatments with one or more other therapeutic agents, including agents normally utilized for the particular therapeutic purpose for which the antibody is being administered, notably for the treatment of a PTCL. The additional therapeutic agent will normally be administered in amounts and treatment regimens typically used for that agent in a monotherapy for the particular disease or condition being treated. Such therapeutic agents include, but are not limited to, anti-inflammation agents, steroids, immune system suppressors, antibiotics, antivirals and other antibodies and fragments thereof.

For example, a second therapeutic agent may include one or more chemotherapeutic drugs, tumor vaccines, antibodies, etc. Further anti-cancer agents include alkylating agents, cytotoxic antibiotics such as topoisomerase I inhibitors, topoisomerase II inhibitors, plant derivatives, RNA/DNA antimetabolites, and antimitotic agents. Examples may include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, taxol, gemcitabine, navelbine, transplatinum, 5-fluorouracil, vincristine, vinblastine and methotrexate, or any analog or derivative variant of the foregoing.

Drugs currently used or tested for the treatment of PTCL include, inter alia, chemotherapeutic agents such as CHOP (cyclophosphamide, doxorubicin, vincristine and prednisone), anthracycline, antifolates, conjugates such as anti-CD25 fused to pseudomonas toxin, IL-2 targeting domain fused with diphtheria toxin, and anti-CD30 antibody conjugated to auristatins (monomethylauristatin-E), HDAC inhibitors, lenalidomide, monoclonal antibodies such as anti-CD52, anti-VEGF (bevacizumab), anti-CD30 (adcetris), anti-CCR4, anti-CD4 (e.g., zanolimumab) and anti-CD2, nucleoside analogues such as cladribine, clofarabine, fludarabine, gemcitabine, nelarabine and pentostatin, proteosome inhibitors such as bortezomib and signaling inhibitors such as selective inhibitors of protein kinase C (e.g., enzastaurin) or syk inhibitors (e.g., R788).

In the treatment methods, the NKp46-binding compound and the second therapeutic agent can be administered separately, together or sequentially, or in a cocktail. In some embodiments, the antigen-binding compound is administered prior to the administration of the second therapeutic agent. For example, the NKp46-binding compound can be administered approximately 0 to 30 days prior to the administration of the second therapeutic agent. In some embodiments, an NKp46-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, an NKp46-binding compound is administered concurrently with the administration of the therapeutic agents. In some embodiments, an NKp46-binding compound is administered after the administration of the second therapeutic agent. For example, an NKp46-binding compound can be administered approximately 0 to 30 days after the administration of the second therapeutic agent. In some embodiments, an NKp46-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

EXAMPLES

Example 1—Anti-NKp46 mAbs are Capable of Directing ADCC Toward NKp46+ Cells

Antibody 195314, mIgG2b, available commercially from R&D Systems, Inc. (Minneapolis, USA) was tested for the ability to mediate ADCC towards the 721.221 EBV transfected B cell line transfected with human NKp46, in comparison with anti-CD20 antibody rituximab.

Briefly, the cytolytic activity of human NK cell line KHYG-1 transfected with murine FcγRIV was assessed in a classical 4-h $^{51}$Cr-release assay in 96-well plates from Greiner. Briefly, 721.221 cells were labelled with $^{51}$Cr (100 pCi (3.7 MBq)/1×10$^6$ cells), then mixed with KHYG-1 transfected with murine FcγRIV (to bind mIgG2b) at an effector/target ratio equal to 20, in the presence of antibody at indicated concentrations. After brief centrifugation and 4 hours of incubation at 37° C., 50 μL supernatant were removed, and the $^{51}$Cr release was measured with a TopCount NXT beta detector (PerkinElmer Life Sciences, Boston, Mass.). All experimental groups were analyzed in triplicate, and the percentage of specific lysis was determined as follows: 100×(mean cpm experimental release–mean cpm spontaneous release)/(mean cpm total release–mean cpm spontaneous release). Percentage of total release was obtained by lysis of target cells with 2% Triton X100 (Sigma).

Antibody 195314 (as well as positive control rituximab) induced specific lysis of NKp46-transfected 721.221 cells by human KHYG-1 murine FcγRIV NK cell lines, thereby showing that these anti-NKp46 antibodies induce ADCC toward NKp46-expressing target cells (FIG. 1). We therefore show that antiNKp46 antibodies with constant regions that bind to activating Fc receptors can lead to depletion of NKp46-expressing tumor cells, and moreover despite KHYG-1 NK cells themselves expressing NKp46 at their surface.

Example 2—NKp46 is Expressed in PTCL

Tumor biopsies were obtained and staining was performed on frozen samples. NKp46 was detected with anti-human NKp46 antibody clone "9E2" (mIgG1), Becton Dickinson, Franklin Lakes, N.J., USA, product ref. 557911, by DAB chromogenic detection according to standard protocols, adapted for immunostaining with BenchMark XT, Ventana Roche. For all staining control isotype (mIgG1) and control DAB were performed. CD30 was additionally stained. Tumors 3, 4 and 5 were from the same patient. Tumors 1-5 were from patients having PTCL not otherwise specified. Tumors 6-8 are mycosis fungoides samples, a cutaneous T cell lymphoma (CTCL).

Tumor characteristics are shown in Table A. Results are shown in Table B. PTCL from each of the samples from the patient from whom tumor samples 3, 4 and 5 were obtained had strong membranar staining, with a high percentage of cells being NKp46 positive. The patient from whom samples 3-5 were obtained had advanced (stage IV) disease. On the other hand, samples 1, 2, 6, 7 and 8 representing less advanced disease (stage I or II) all had either no staining or low percentages of NKp46+ tumor cells. Consequently, while some tumors are capable of expressing NKp46 at high levels and are thus suitable for targeting with an NKp46 binding agent, tumor cells may acquire the NK marker NKp46 at more advanced stages of disease, or more aggressive disease. NKp46 may therefore be a particularly suitable target for treatment of advanced disease, or for preventing progression of disease to advanced stages. Additionally, treatment of earlier stage disease with an NKp46 binding agent may benefit from diagnostic (e.g., theranostic) assays to identify patients having prominent expression of NKp46 on the surface of tumor cells. The NKp46 positive tumors were CD30-negative; NKp46 may therefore furthermore represent a therapeutic target when anti-CD30 antibodies cannot be used (or when tumors are resistant to anti-CD30 antibody).

Example 3—NKp46 is Expressed in Samples from ALCL and Ortho Visceral Extranodal Disease (NK/T-Lymphoma and EATL)

MEC04 and SNK6 NK/T-lymphoma cells were stained for NKp46 expression using flow cytometry (FACS), together with characterization of various cell surface markers. NKp46 was stained with anti-NKp46 antibody linked to phycoerythrin (PE). Additional markers evaluated were hCD56 PE, hCD183/CXCR3 PE, hCD3 PE, hCD4 PE, hCD8 PE and CD54/ICAM PE. Cells were harvested and stained using PE-labeled antibodies. After two washes, stainings were acquired on a BD FACSCanto II and analyzed using the FlowJo software.

Figure 2:
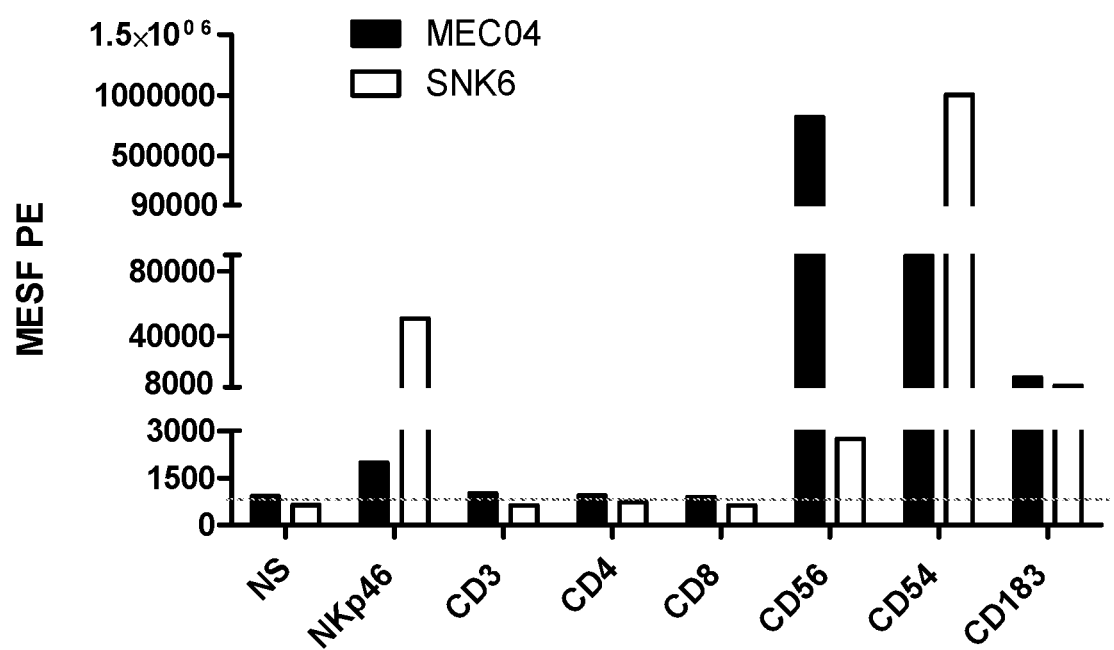
FIG. 2 shows staining by anti-NKp46 antibody on NK−/T-lymphoma cells. The figure additionally shows that the NKp46-positive cells express CD183 (CXCR3), CD56 and CD54 (ICAM).

Results are shown in FIG. 2. Anti-NKp46 antibody showed staining on the MEC04 and SNK6 cells, although with greater expression on SNK6. MEC04 and SNK6 cells were additionally strongly stained with CD183 (CXCR3), CD56 and CD54 (ICAM), but not CD3, CD4 or CD8 (the most common phenotype of extranodal NK/T-lymphomas are surface CD3- and CD56+).

We show that NK/T lymphoma cells, and in particular extranodal NK/T-cell lymphoma, nasal type, can express NKp46, thereby providing the possibility to treat NK/T- lymphoma with anti-NKp46 antibodies. Additionally, NKp46-positive NK/T-lymphoma tumors were found to NKp46. Of the ALCL that stained positive for NKp46, 2 samples were ALK+ while one was ALK−.

TABLE A

| Sample | Tissue type | Appearance | Pathology diagnosed | Tumor stage (minimum) | % normal | % lesion | % tumor | % necrosis |
|---|---|---|---|---|---|---|---|---|
| 1 | Lymphoid tissue/lymphatic ganglion | Tumoral | PTCL (unspecified) | I | 5 | 0 | 90 | 0 |
| 2 | Lymphoid tissue/testicle | Tumoral | PTCL-NOS (unspecified) | IE | 10 | 0 | 60 | 0 |
| 3 | Lymphoid tissue/spleen | Tumoral | PTCL-NOS (unspecified) | IV | 10 | 0 | 40 | 0 |
| 4 | Lymphoid tissue/spleen | Tumoral | PTCL-NOS (unspecified) | IV | 5 | 0 | 90 | 0 |
| 5 | Lymphoid tissue/spleen | Tumoral | PTCL-NOS (unspecified) | IV | 50 | 0 | 50 | 0 |
| 6 | Lymphoid tissue/lymphatic ganglion | Tumoral | Mycosis fungoides | II | 0 | 0 | 70 | 20 |
| 7 | Lymphoid tissue/lymphatic ganglion | Tumoral | Mycosis fungoides | II | 0 | 0 | 80 | 10 |
| 8 | Lymphoid tissue/lymphatic ganglion | Tumoral | Mycosis fungoides | II | 0 | 0 | 80 | 10 |

TABLE B

| | Tumor 1: LN Lymphoma peripheral T cells | Tumor 2: testis Lymphoma peripheral T cells | Tumor 3: spleen Lymphoma peripheral T cells | Tumor 4: spleen Lymphoma peripheral T cells | Tumor 5: spleen Lymphoma peripheral T cells | Tumor 6: LN Mycosis fungoides | Tumor 7: LN Mycosis fungoides | Tumor 8: LN Mycosis fungoides |
|---|---|---|---|---|---|---|---|---|
| NKp46 Staining | Negative | 20% positive | 70% positive | 80% positive | 70-80% positive | 10% faintly positive | 10% faintly positive | <5% faintly positive |
| NKp46 Stained areas/ comments | Less than 2% positive cells. Membrane and paranuclear dot staining of low intensity (probably infiltrating NK cells) | Low intensity membrane and paranuclear dot staining | Membrane and paranuclear dot staining | Membrane staining | Membrane staining | Faint membrane staining + diffused and fuzzy focal staining | Faint membrane staining + diffused and fuzzy focal staining | Faint membrane staining |
| CD30 Staining | 30% positive | Negative | Negative | Negative | Negative | 95% positive | 95% positive | 95% positive |
| CD30 Stained areas/ comments | paranuclear dot staining | | | | | Cytoplasmic with paranuclear dot staining | Membrane and cytoplasmic with paranuclear dot staining | Membrane and cytoplasmic with paranuclear dot staining | express CD183 (CXCR3), CD56 and CD54 (ICAM), which may permit administration of anti-NKp46 in poor-prognosis patients, notably those having CXCR3 expression typically associated with poor disease prognosis.

Studies were then carried out by immunohistochemistry (IHC) to provide confirmation on patient samples and for different indications, by staining primary tumor cells from human patients in frozen tissue sections with labeled anti-NKp46 antibody. Briefly, cell lines known to be positive and negative for NKp46 expression were used as positive and negative controls, respectively. Next, frozen hematopoietic tissues sections from healthy donors were stained for NKp46 expression, all of which were negative for NKp46 expression. In NK/T lymphomas, nasal type, 6 patient samples were tested, of which 5 samples were interpretable. All 5 interpretable samples were positively stained, confirming that NK/T-lymphomas express NKp46. In samples from patients diagnosed with enteropathy-associated T-cell lymphoma (EATL), of 6 patient samples, 5 samples were interpretable, of which in turn 2 were positively stained and 3 were negative for staining, confirming that EATL cells can express NKp46. In samples from patients diagnosed with anaplastic large cell lymphoma (ALCL), of 4 interpretable patient samples, 3 were positively stained and 1 was negative for staining, confirming that ALCL cells can express All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a", "an", "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having", "including", or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples or exemplary language (e.g., "such as") provided herein is intended merely to better illuminate the invention and does not impose a limitation on the scope of the invention unless otherwise claimed. No language in the specification should be construed as indicating any non-claimed element as essential to the practice of the invention.

We claim:

1. A method for detecting NKp46 expression in an individual having refractory celiac disease (RCD) and treating said individual comprising:
   a) obtaining a biological sample from the individual, said biological sample comprising RCD cells, contacting said RCD cells with an antibody that binds NKp46 polypeptide, and detecting NKp46 polypeptide expression on the surface of said cells; and
   b) treating individuals expressing NKp46 polypeptide on RCD cells with anti-NKp46 antibodies.

* * * * *

UNITED STATES PATENT AND TRADEMARK OFFICE
CERTIFICATE OF CORRECTION

PATENT NO. : 11,999,784 B2
APPLICATION NO. : 16/451051
DATED : June 4, 2024
INVENTOR(S) : Cécile Bonnafous et al.

Page 1 of 1

It is certified that error appears in the above-identified patent and that said Letters Patent is hereby corrected as shown below:

In the Specification

Column 11,
Line 22, "(e.g., a, b, E and p for" should read --(e.g., α, δ, ε and μ for--.

Column 24,
Line 4, "Silver-ill" should read --Silver-111--.
Line 30, "FcγRII (CD 16)" should read --FcγRIII (CD 16)--.
Line 34, "FcγRIIa" should read --FcγRIIIa--.

Column 27,
Line 13, "FcγRII" should read --FcγRIII--.

Column 31,
Lines 54-55, "CD4+ and CD8-" should read --$CD4^+$ and $CD8^-$--.

Column 35,
Line 47, "pCi" should read --μCi--.

Signed and Sealed this
First Day of July, 2025

Coke Morgan Stewart
*Acting Director of the United States Patent and Trademark Office*